(12) United States Patent
Wack et al.

(10) Patent No.: US 9,237,887 B2
(45) Date of Patent: Jan. 19, 2016

(54) TISSUE ENGAGING MEMBER

(75) Inventors: Michael A. Wack, Warsaw, IN (US); Kevin T. Stone, Winona Lake, IN (US); Gregory J. Denham, Warsaw, IN (US)

(73) Assignee: BIOMET SPORTS MEDICINE, LLC, Warsaw, IN (US)

( * ) Notice: Subject to any disclaimer, the term of this patent is extended or adjusted under 35 U.S.C. 154(b) by 364 days.

(21) Appl. No.: 13/111,474

(22) Filed: May 19, 2011

(65) Prior Publication Data

US 2012/0296345 A1 Nov. 22, 2012

(51) Int. Cl.
*A61B 17/04* (2006.01)
*A61F 2/08* (2006.01)
*A61B 17/00* (2006.01)
*A61B 17/11* (2006.01)
*A61B 17/06* (2006.01)

(52) U.S. Cl.
CPC ......... *A61B 17/0401* (2013.01); *A61B 17/0483* (2013.01); *A61F 2/0811* (2013.01); *A61B 17/1146* (2013.01); *A61B 2017/00889* (2013.01); *A61B 2017/042* (2013.01); *A61B 2017/044* (2013.01); *A61B 2017/0406* (2013.01); *A61B 2017/047* (2013.01); *A61B 2017/0409* (2013.01); *A61B 2017/0412* (2013.01); *A61B 2017/0414* (2013.01); *A61B 2017/0417* (2013.01); *A61B 2017/0429* (2013.01); *A61B 2017/0437* (2013.01); *A61B 2017/0441* (2013.01); *A61B 2017/0446* (2013.01); *A61B 2017/0464* (2013.01); *A61B 2017/0496* (2013.01); *A61B 2017/06176* (2013.01); *A61F 2002/0841* (2013.01); *A61F 2002/0852* (2013.01); *A61F 2002/0888* (2013.01); *A61F 2220/0016* (2013.01)

(58) Field of Classification Search
USPC ......................................................... 606/232
See application file for complete search history.

(56) References Cited

U.S. PATENT DOCUMENTS

| | | | |
|---|---|---|---|
| 3,003,155 A * | 10/1961 | Mielzynski et al. | 623/15.11 |
| 5,037,422 A | 8/1991 | Hayhurst et al. | |
| 5,100,417 A * | 3/1992 | Cerier et al. | 606/139 |
| 5,224,946 A * | 7/1993 | Hayhurst et al. | 606/232 |
| 5,236,431 A * | 8/1993 | Gogolewski et al. | 606/139 |
| 5,370,662 A * | 12/1994 | Stone et al. | 606/232 |
| 5,383,905 A * | 1/1995 | Golds et al. | 606/232 |
| 5,417,691 A | 5/1995 | Hayhurst | |
| 5,500,000 A * | 3/1996 | Feagin et al. | 606/232 |
| 5,522,843 A * | 6/1996 | Zang | 606/232 |
| 5,584,835 A * | 12/1996 | Greenfield | 606/232 |
| 5,601,557 A * | 2/1997 | Hayhurst | 606/232 |
| 5,690,676 A * | 11/1997 | DiPoto et al. | 606/232 |
| 5,733,307 A * | 3/1998 | Dinsdale | 606/232 |
| 5,782,865 A * | 7/1998 | Grotz | 606/232 |
| 6,290,702 B1 * | 9/2001 | Fucci et al. | 606/323 |

(Continued)

OTHER PUBLICATIONS

"SportMesh Soft Tissue Reinforcement", ARTHROTECK® A Biomet Company brochure, pp. 1-4 (2006).

(Continued)

*Primary Examiner* — Dianne Dornbusch
(74) *Attorney, Agent, or Firm* — Schwegman Lundberg & Woessner, P.A.

(57) ABSTRACT

A system includes a flexible member and a tissue engaging member fixed to the flexible member. The tissue engaging member includes a barb preformed to extend rearward from a distal end of the flexible member at an acute angle relative to the flexible member.

29 Claims, 16 Drawing Sheets

(56) References Cited

U.S. PATENT DOCUMENTS

| | | | |
|---|---|---|---|
| 6,616,694 B1* | 9/2003 | Hart | 623/13.14 |
| 6,632,245 B2* | 10/2003 | Kim | 623/13.14 |
| 6,641,596 B1* | 11/2003 | Lizardi | 606/232 |
| 7,217,279 B2* | 5/2007 | Reese | 606/232 |
| 7,500,983 B1 | 3/2009 | Kaiser et al. | |
| 7,572,265 B2 | 8/2009 | Stone et al. | |
| 7,601,165 B2 | 10/2009 | Stone | |
| 7,658,751 B2 | 2/2010 | Stone et al. | |
| 7,780,701 B1* | 8/2010 | Meridew et al. | 606/232 |
| 2002/0087190 A1* | 7/2002 | Benavitz et al. | 606/232 |
| 2002/0161401 A1* | 10/2002 | Steiner | 606/232 |
| 2003/0018358 A1* | 1/2003 | Saadat | 606/232 |
| 2003/0088272 A1* | 5/2003 | Smith | 606/232 |
| 2003/0176865 A1* | 9/2003 | Supinski | 606/72 |
| 2004/0093031 A1* | 5/2004 | Burkhart et al. | 606/232 |
| 2004/0133239 A1* | 7/2004 | Singhatat | 606/232 |
| 2005/0033367 A1* | 2/2005 | Leung et al. | 606/232 |
| 2005/0203620 A1* | 9/2005 | Steiner et al. | 623/13.14 |
| 2005/0245932 A1* | 11/2005 | Fanton et al. | 606/72 |
| 2006/0089711 A1* | 4/2006 | Dolan | 623/2.37 |
| 2006/0189993 A1* | 8/2006 | Stone | 606/73 |
| 2007/0038230 A1 | 2/2007 | Stone et al. | |
| 2007/0179510 A1 | 8/2007 | Stone | |
| 2007/0225735 A1 | 9/2007 | Stone et al. | |
| 2008/0082127 A1 | 4/2008 | Stone et al. | |
| 2008/0082128 A1* | 4/2008 | Stone | 606/232 |
| 2008/0234731 A1* | 9/2008 | Leung et al. | 606/232 |

OTHER PUBLICATIONS

Ti Screw Suture Anchor Brochure, Biomet Sports Medicine, 1 page (2012).

* cited by examiner

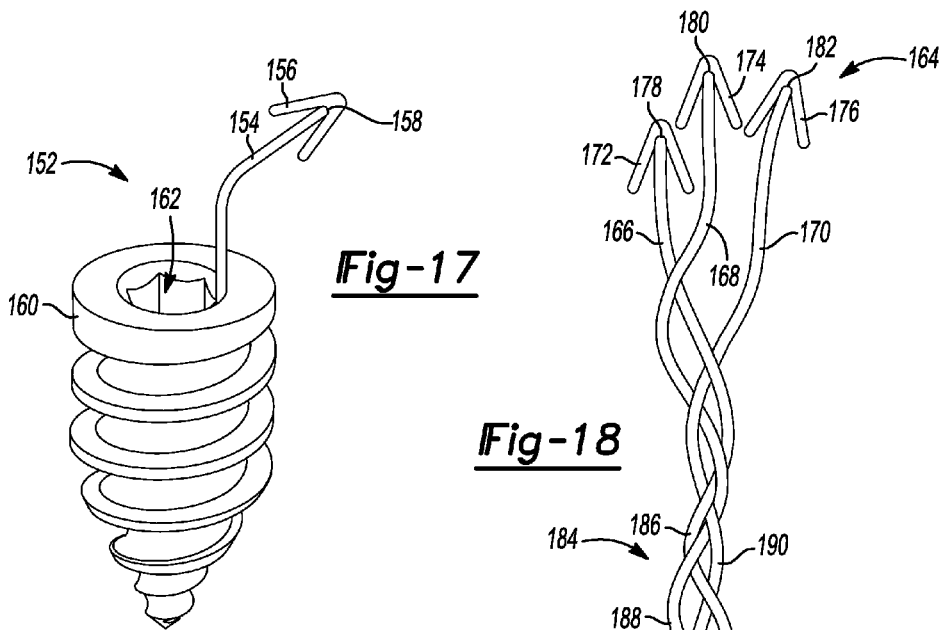
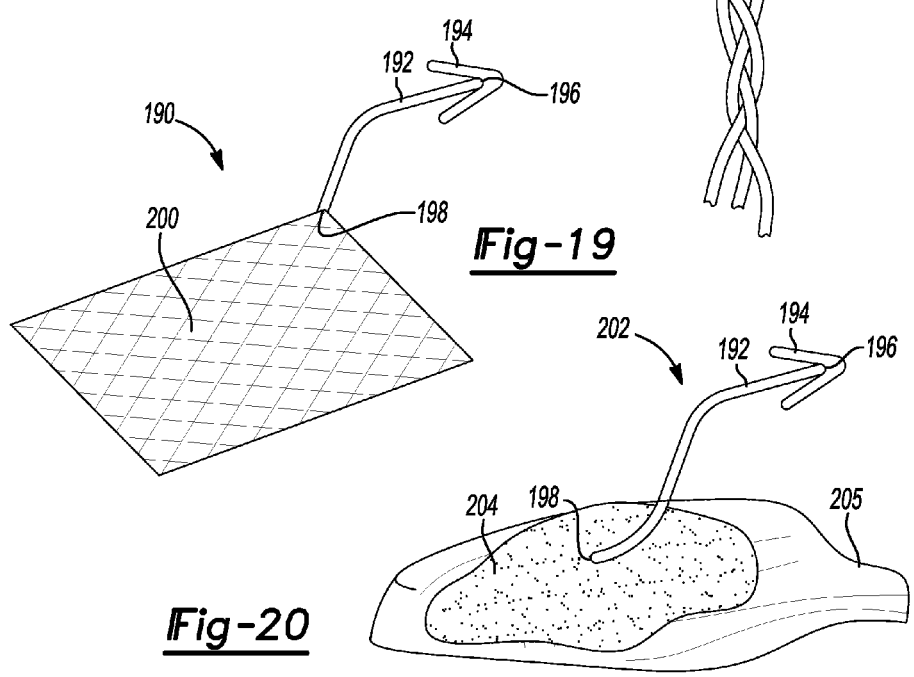

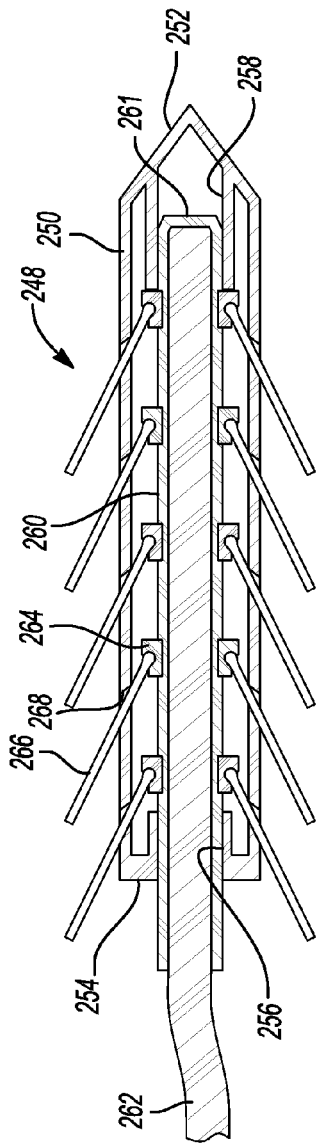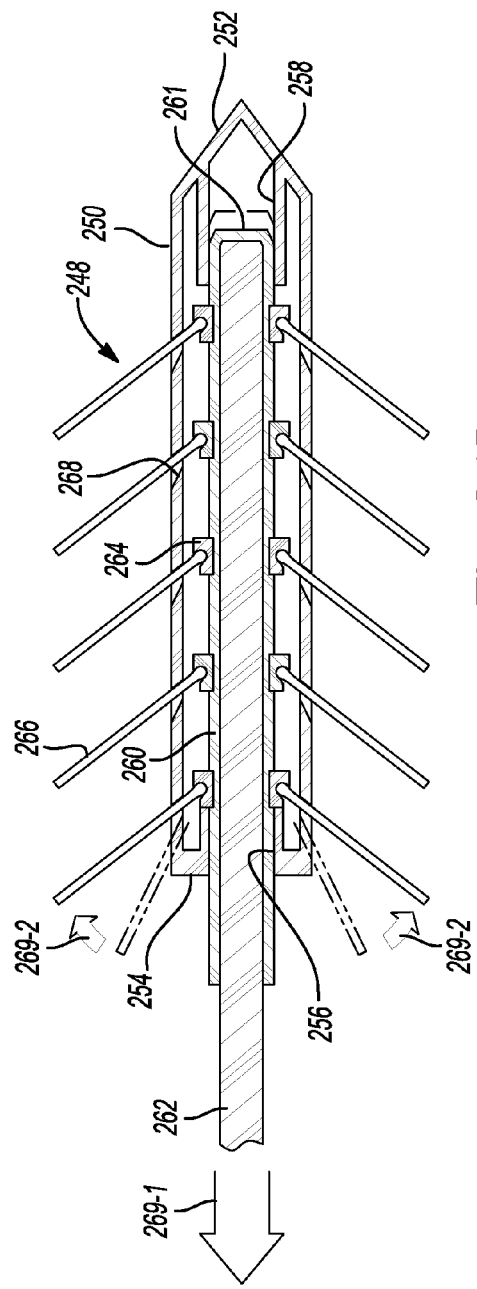

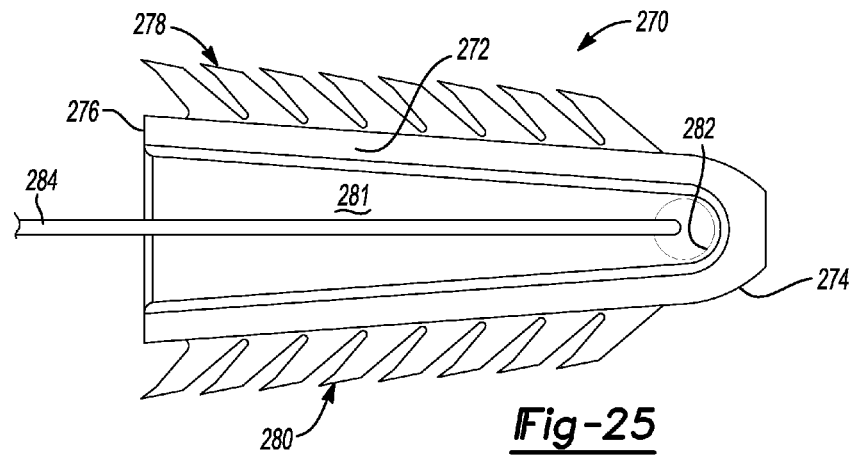
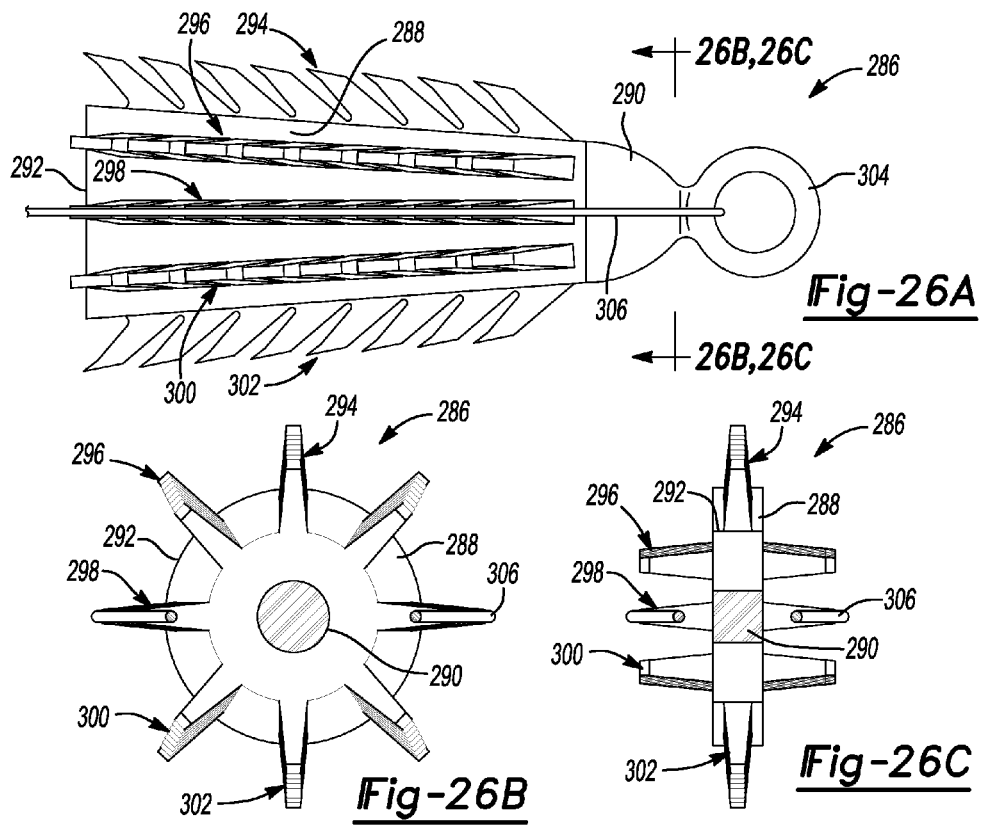

TISSUE ENGAGING MEMBER

FIELD

The present disclosure relates to tissue engaging members attached to flexible or elongate members configured to be inserted into tissue.

BACKGROUND

This section provides background information related to the present disclosure which is not necessarily prior art.

In tissue repairs such as rotator cuff repairs and anterior cruciate ligament (ACL) reconstructions, a suture is typically used to attach soft tissue to bone or to other soft tissue. The soft tissue can be a tendon, a ligament, or cartilage. The suture can be used to hold soft tissue by wrapping the suture around soft tissue or passing the suture through soft tissue. The suture can be attached to bone using a suture anchor. Using knots to attach the suture to soft tissue or to bone may add complexity and time to the procedure.

Accordingly, the present disclosure describes a tissue engaging member that can be attached to a flexible member, such as a suture, or to an elongate member. The tissue engaging member alone can be used as a knotless suture anchor, or the tissue engaging member attached to the elongate member can be used as a knotless suture anchor. The tissue engaging member includes one or more barbs that deflect radially inward to allow insertion of the tissue engaging member into tissue and that deflect radially outward to prevent removal of the tissue engaging member from tissue.

SUMMARY

This section provides a general summary of the disclosure, and is not a comprehensive disclosure of its full scope or all of its features.

A system includes a flexible member and a tissue engaging member fixed to the flexible member. The tissue engaging member includes a barb preformed to extend rearward from a distal end of the flexible member at an acute angle relative to the flexible member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 17 is a perspective view of a tissue engaging member attached to a distal end of a flexible member and a suture anchor attached to a proximal end of the flexible member;

FIG. 18 is a perspective view of a plurality of flexible members having portions that are intertwined and distal ends to which tissue engaging members are attached;

FIG. 19 is a perspective view of a tissue engaging member attached to a distal end of a flexible member and a tissue reinforcing material attached to a proximal end of the flexible member;

FIG. 20 is a perspective view of a tissue engaging member attached to a distal end of a flexible member and a tissue adhering material attached to a proximal end of the flexible member;

FIG. 24A is a section view of a fourth elongate member including an actuator coupled to a distal end of a suture and pivotally connected to a plurality of tissue engaging members;

FIG. 24B is a section view of the fourth elongate member of FIG. 24A, with the suture retracted to retract the actuator and thereby extend the tissue engaging members radially outward from the fourth elongate member;

FIG. 25 is a planar view of a fifth elongate member including a plurality of tissue engaging members extending rearward from a distal end of an elongate body, where the tissue engaging members are absent from surfaces of the elongate body adjacent to a hole through which a suture is passed;

FIG. 26A is a planar view of a sixth elongate member including a plurality of tissue engaging members extending rearward from a distal end of an elongate body and an suture engaging feature attached to the distal end of the elongate body;

FIG. 26B is a section view of a first embodiment of the sixth elongate member of FIG. 26A including an elongate body having a round shape.

FIG. 26C is a section view of a second embodiment of the sixth elongate member of FIG. 26B including an elongate body having a flat shape.

Figure 39:
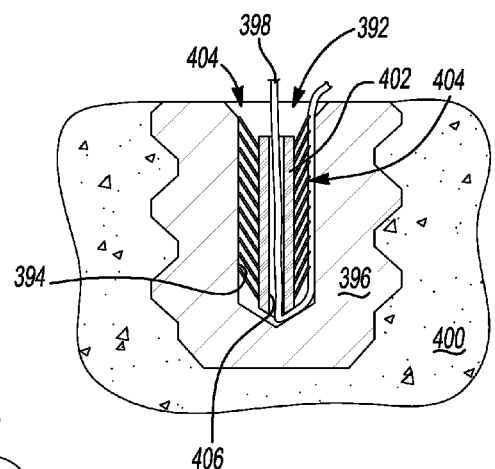
Figure 40:
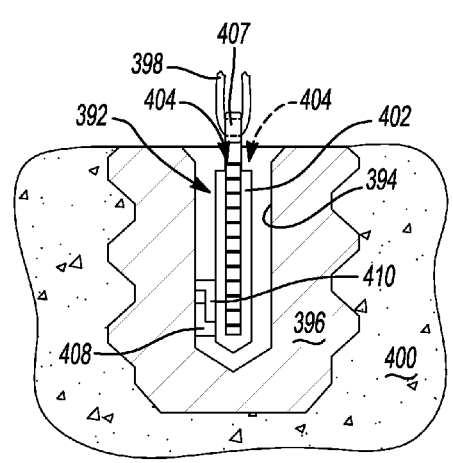

FIG. 39 is a planar view of an elongate member being inserted into a proximal end of a cannulated suture anchor fixed in tissue, a distal end of the elongate member including a suture engaging feature through which a suture is passed, the elongate member including a plurality of tissue engaging members for engaging the cannulated suture anchor to fix the suture to tissue; and FIG. 40 is a planar view of an elongate member being inserted through a proximal end of a cannulated suture anchor fixed in tissue, a distal end of the elongate member including a suture engaging feature through which a suture is passed, where the elongate member can be rotated to engage a bracket on the elongate member with a bracket on the cannulated suture anchor.

Corresponding reference numerals indicate corresponding parts throughout the several views of the drawings.

DESCRIPTION OF VARIOUS EMBODIMENTS

Example embodiments will now be described more fully with reference to the accompanying drawings.

Figure 1:
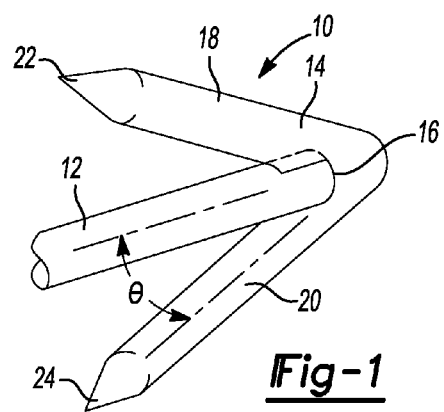
FIG. 1 is a perspective view of a first tissue engaging member attached to a distal end of a flexible member.

Referring now to FIG. 1, a system 10 includes a suture or flexible member 12 and a tissue engaging member 14. The flexible member 12 can be monofilament, multifilament, and/or braided and can be coated with antimicrobials. The tissue engaging member 14 is fixed to a distal end 16 of the flexible member 12. The flexible member 12 and the tissue engaging member 14 can be formed integrally as a single unit, such as by molding the flexible member 12 and the tissue engaging member 14 in a single operation, or the flexible member 12 and the tissue engaging member 14 can be formed separately and later joined together. The tissue engaging member 14 can be molded to the flexible member 12, press fit to the flexible member 12, or fixed to the flexible member 12 using an adhesive or otherwise fixing or connecting structure.

The tissue engaging member 14 includes a first barb 18 and a second barb 20 that are preformed to extend rearward from the distal end 16 of the flexible member 12 at an acute angle θ relative to the flexible member 12. The first and second barbs 18, 20 can be 0.5 to 2.0 millimeters (mm) in diameter and 2.0 to 6.0 mm in length. The first barb 18 has a distal end 22, and the second barb 20 has a distal end 24. The distal ends 22, 24 of the tissue engaging member 14 can be sharpened, as shown, or rounded. The flexible member 12 can be made from a first material, and the tissue engaging member 14 can be made from a second material. The second material can be the same as the first material, or the second material can be different from and/or stiffer than the first material. The first material can be polyethylene, and the second material can be polyether ether ketone (PEEK) and/or metal.

When the distal end 16 of the flexible member 12 is inserted into tissue in a first direction, the barbs 18, 20 may deflect radially inward toward the flexible member 12 to reduce the effort required to insert the flexible member 12 into the tissue. Once the distal end 16 of the flexible member 12 is inserted into the tissue, the tissue engaging member 14 maintains the distal end 16 of the flexible member 12 in the tissue. If tension is applied to the flexible member 12 in a second opposite direction, the barbs 18, 20 may deflect radially outward from the flexible member 12 and the distal ends 22, 24 of the barbs 18, 20 pierce into tissue to prevent easy removal of the flexible member 12 from the tissue. In this manner, the tissue engaging member 14 attaches to and bites into the tissue. The barbs 18, 20 may deflect when the flexible member 12 is inserted into or pulled from tissue such as bone, and the barbs 18, 20 may not deflect when the flexible member 12 is inserted into or pulled from tissue such as soft tissue.

Figure 2:
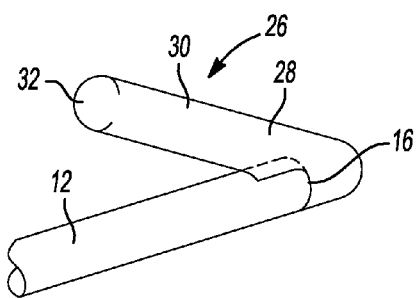
FIG. 2 is a perspective view of a second tissue engaging member attached to a distal end of a flexible member.
Figure 3:
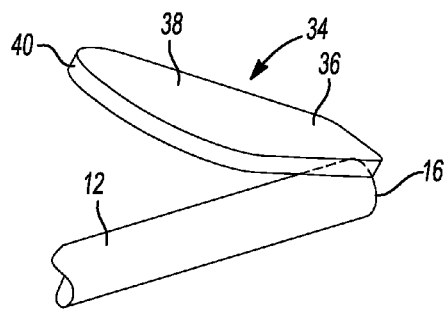
FIG. 3 is a perspective view of a third tissue engaging member attached to a distal end of a flexible member.
Figure 4:
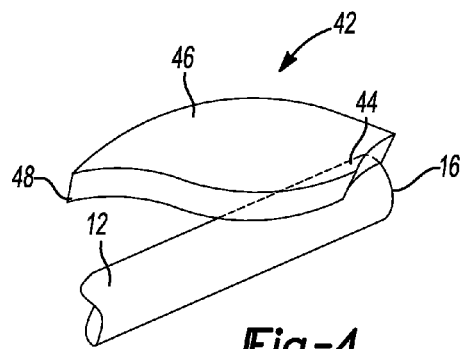
FIG. 4 is a perspective view of a fourth tissue engaging member attached to a distal end of a flexible member.

With continued reference to FIG. 1 and additional reference to FIGS. 2 through 4, a tissue engaging member according to the present disclosure can include one or more barbs having various shapes and sizes. FIG. 1 shows that the barbs 18, 20 of the tissue engaging member 14 are cylindrical, are opposed, and are joined together to form an arrow shape. FIG. 2 shows a system 26 including the flexible member 12 and a tissue engaging member 28 includes a barb 30 having a cylindrical shape and extending rearward from the distal end 16 of the flexible member 12. The barb 30 has a distal end 32 that can be relatively flat, rounded, or sharpened.

FIG. 3 shows a system 34 including the flexible member 12 and a tissue engaging member 36. The tissue engaging member 36 includes a barb 38 having a fish-scale shape and oval-shaped planar faces with only one axis of symmetry. The barb 38 has a distal end 40 including generally arcuate edges transitioning to generally straight edges that taper inward as they extend from the distal end 40 of the barb 38 to the distal end 16 of the flexible member 12.

FIG. 4 shows a system 42 including the flexible member 12 and a tissue engaging member 44. The tissue engaging member 44 includes a barb 46 that is shaped similar to a claw or a prey-catching tooth. The barb 46 has generally rounded major surfaces and generally arcuate edges. The barb 46 includes a distal end 48 that is pointed or sharp and can pierce into tissue. The generally arcuate edges of the barb 46 taper outward from the distal end 48 of the barb 46 to the longitudinal center of the barb 46, and taper inward from the longitudinal center of the barb 46 to the distal end 16 of the flexible member 12.

Figure 5:
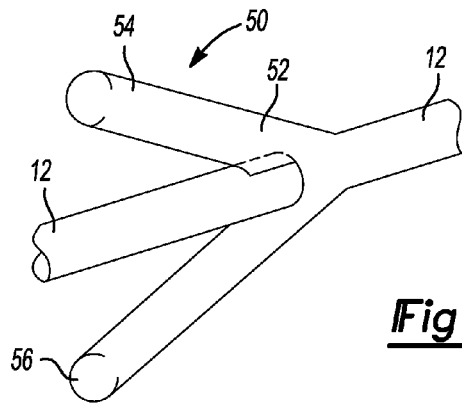
FIG. 5 is a perspective view of a flexible member passing through a tissue engaging member.

With continued reference to FIG. 1 and additional reference to FIGS. 5 through 8, the flexible member 12 can extend through or terminate at a tissue engaging member according to the principles of the present disclosure. FIG. 1 shows the flexible member 12 terminating at the tissue engaging member 14. FIG. 5 shows a system 50 including a tissue engaging member 52 through which the flexible member 12 is passed. The tissue engaging member 52 includes a first barb 54 and a second barb 56 attached to the flexible member 12. The barbs 54, 56 can be separate pieces or can be a single piece including a hole through which the flexible member 12 is passed.

Figure 6:
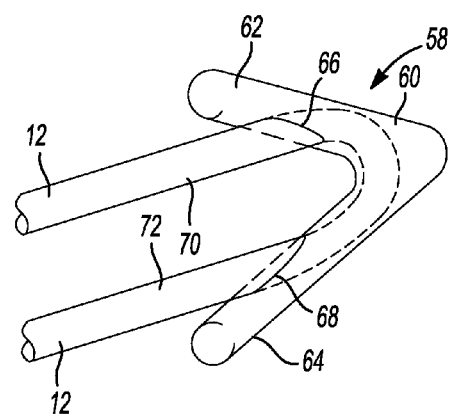
FIG. 6 is a perspective view of a flexible member entering a proximal surface of a tissue engaging member, passing through the tissue engaging member, and exiting the proximal surface of the tissue engaging member.

FIG. 6 shows a system 58 including the flexible member 12 and a tissue engaging member 60. The tissue engaging member 60 includes a first barb 62 and a second barb 64 that are joined together to form an arrow shape. The flexible member 12 enters the tissue engaging member 60 at an entry position 66 on the first barb 62, and the flexible member 12 exits the tissue engaging member 60 at an exit position 68 on the second barb 64. The tissue engaging member 60 can include holes at the entry and exit positions 66, 68 through which the flexible member 12 can be passed through. The flexible member 12 can be secured to the tissue engaging member 60 or the flexible member 12 can be allowed to move relative to the tissue engaging member 60. The flexible member 12 includes a first portion 70 that extends in a first direction toward the tissue engaging member 60, and a second portion 72 that extends in a second direction away from the tissue engaging member 60. The second direction is generally opposite from the first direction.

Figure 7:
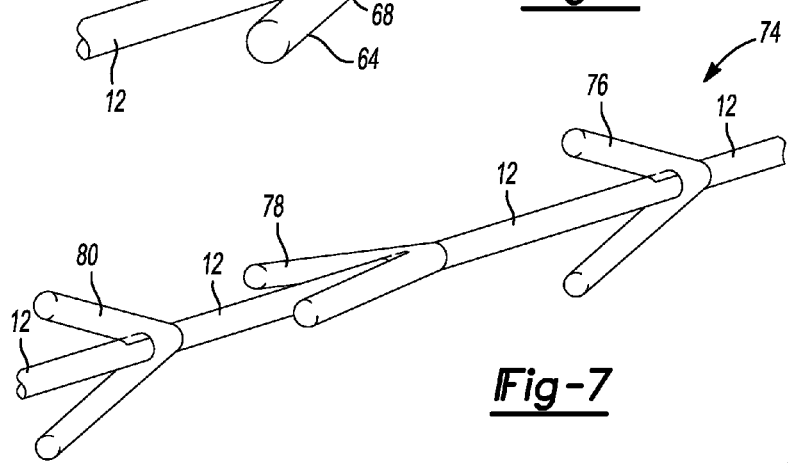
FIG. 7 is a perspective view of a flexible member passing through a plurality of tissue engaging members.

FIG. 7 shows a system 74 shaped similar to a wire or bristle brush and including the flexible member 12 and tissue engaging members 76, 78, 80. The tissue engaging members 76, 78, 80 each include two barbs that form an arrow shape and extend rearward from the distal end 16 of the flexible member 12 (shown in FIG. 1). The tissue engaging members 76, 78, 80 can be randomly or uniformly attached to the flexible member 12 along the length of and about the flexible member 12, including at the distal end 16 of the flexible member 12. The tissue engaging members 76, 78, 80 can include holes through which the flexible member 12 extends, or the barbs forming the tissue engaging members 76, 78, 80 can be separate from each other and attached to the flexible member 12. Also the system 74 can include different tissue engaging members along the length of the flexible member 12, such as those shown in FIGS. 1 through 5, and/or tissue engaging members braided into the flexible member 12.

The tissue engaging member 78 can be rotated 90 degrees around the longitudinal axis of the flexible member 12 relative to the tissue engaging members 76, 80. This ensures that the tissue engaging members 76, 78, 80 extends in one of four radial directions from the flexible member 12, rather than extending in only two radial directions from the flexible member 12. In turn, the pullout force required to remove the tissue engaging members 76, 78, 80 from tissue can be increased. In addition, the tissue engaging members 76, 80 can be used to fix a first set of tissue portions together, and the tissue engaging member 78 can be used to fix a second set of tissue portions together. Multiple tissue engaging members can be oriented like the tissue engaging member 78.

Figure 8:
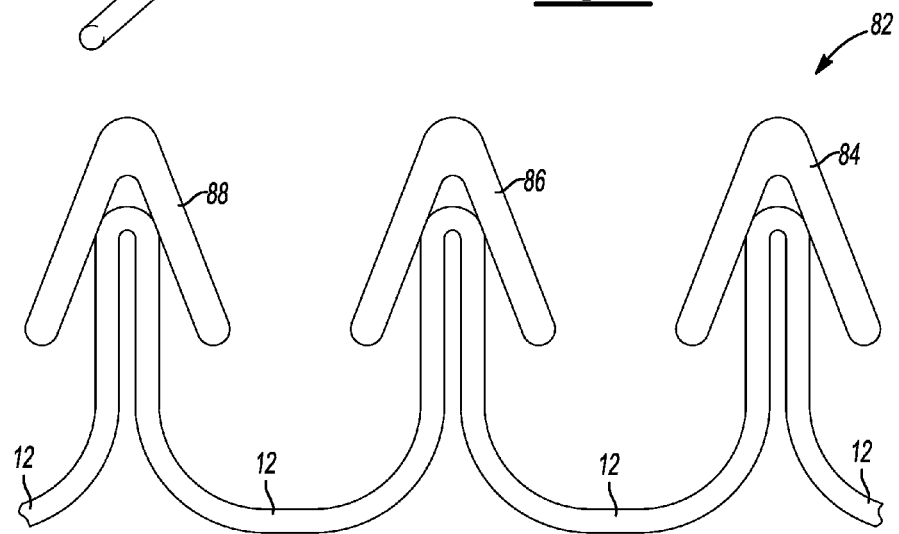
FIG. 8 is a planar view of a flexible member attached to proximal surfaces of a plurality of tissue engaging members.

FIG. 8 shows a system 82 that can be inserted into multiple openings in tissue. The system 82 includes the flexible member 12 and tissue engaging members 84, 86, 88 each having an arrow shape. The flexible member 12 extends toward an inner surface of each of the tissue engaging members 84, 86, 88 in a first direction, is attached to the inner surface of the tissue engaging members 84, 86, 88, and extends away from the tissue engaging members 84, 86, 88 in a second direction that is generally opposite from the first direction. The flexible member 12 can be molded to the tissue engaging members 84, 86, 88 or attached to the tissue engaging members 84, 86, 88 using an adhesive. Additionally, the flexible member 12 can enter and exit holes in each of the tissue engaging members 84, 86, 88, as shown in FIG. 6.

Figure 9:
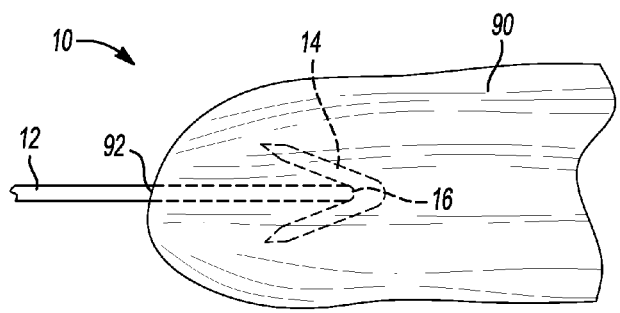
FIG. 9 is a planar view of a tissue engaging member attached to a distal end of a flexible member and inserted into tissue.

Referring now to FIGS. 9 through 14, methods of using the system 10 will now be described. Although the system 10 is shown and described in FIGS. 9 through 14, the methods of use for the system 10 can apply to any of the flexible member systems shown or described in the present disclosure and to any combination thereof. FIG. 9 shows the distal end 16 of the flexible member 12 and the tissue engaging member 14 inserted into a tissue 90. The tissue 90 can be a soft tissue, such as a tendon, a ligament, or cartilage, and the tissue engaging member 14 can be used to fix the tissue 90 to other soft tissue or to bone. The tissue engaging member 14 enters the tissue 90 in a first direction at the location 92 and, without knots, prevents removal of the distal end 16 of the flexible member 12 from the tissue 90 in a second opposite direction. In this regard, the system 10 is unidirectional.

Figure 10:
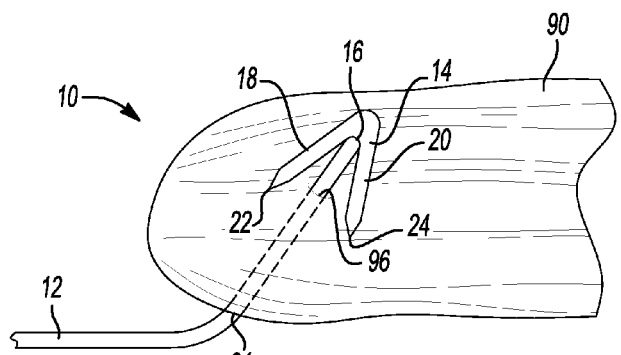
FIG. 10 is a planar view of a tissue engaging member attached to a distal end of a flexible member and passed through a portion of tissue.

FIG. 10 shows the distal end 16 of the flexible member 12 and the tissue engaging member 14 entering the tissue 90 at a location 94, passing through the tissue 90, and exiting the tissue 90 at a location 96. In this position, the distal ends 22, 24 of the tissue engaging member 14 can engage the tissue 90 when a removal or tension force is applied to the flexible member 12. This engagement prevents removal of the flexible member 12 and the tissue engaging member 14 from the tissue 90.

Figure 11:
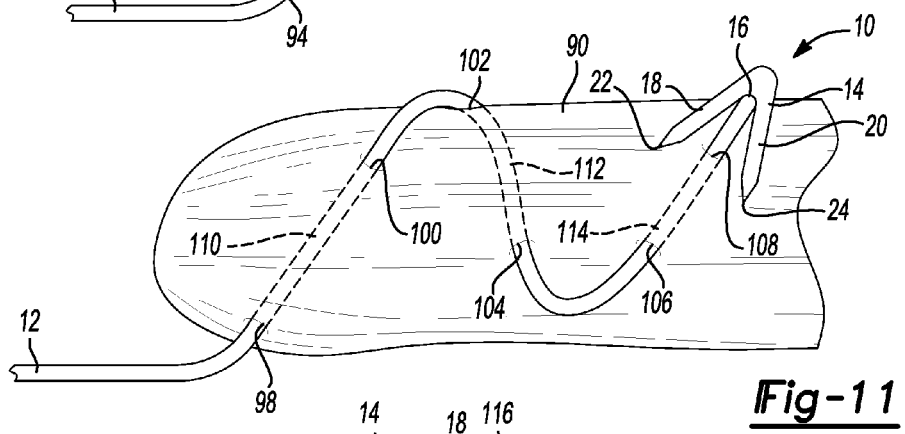
FIG. 11 is a planar view of a tissue engaging member attached to a distal end of a flexible member and passed through several portions of tissue.

FIG. 11 shows the distal end 16 of the flexible member 12 and the tissue engaging member 14 entering and exiting the tissue 90 at several locations in a spiral, helical, or otherwise similar manner. In turn, several portions of the flexible member 12 are embedded in the tissue 90. The distal end 16 of the flexible member 12 and the tissue engaging member 14 enter the tissue 90 at a location 98, exit the tissue 90 at a location 100, enter the tissue 90 at a location 102, exit the tissue 90 at a location 104, enter the tissue 90 at a location 106, and exit the tissue 90 at a location 108. Alternatively, the distal end 16 of the flexible member 12 and the tissue engaging member 14 can terminate in the tissue 90, as shown in FIG. 9.

Portions of the flexible member 12 that are embedded in the tissue 90 include a portion 110, a portion 112, and a portion 114. Since multiple portions of the flexible member 12 are embedded in the tissue 90, the holding capacity of the flexible member 12 can be increased so that a higher tension force can be applied to the flexible member 12 without pulling the flexible member 12 out of the tissue 90. The pullout force of the flexible member 12 can be increased even more by attaching a plurality of tissue engaging members to the flexible member 12 along the length of the flexible member 12, such as shown in FIG. 7.

Figure 12:
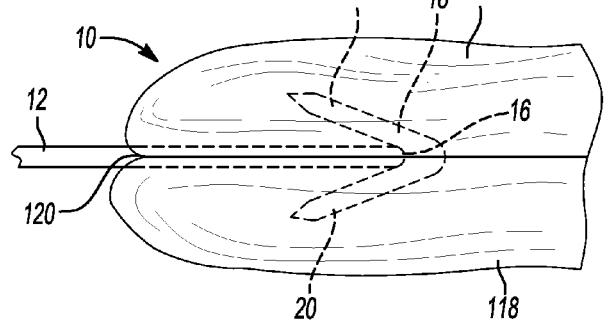
FIG. 12 is a planar view of a tissue engaging member attached to a distal end of a flexible member, with one barb of the tissue engaging member inserted into one portion of tissue and another barb of the tissue engaging member inserted into another portion of tissue.

FIG. 12 shows the distal end 16 of the flexible member 12 and the tissue engaging member 14 inserted between adjacent tissue portions 116, 118. The distal end 16 of the flexible member 12 and the tissue engaging member 14 are inserted between the tissue portions 116, 118 at a location 120. The first barb 18 of the tissue engaging member 14 is engaging the tissue portion 116, and the second barb 20 of the tissue engaging member 14 is engaging the second tissue portion 118. This engagement holds the tissue portions 116, 118 together to, for example, close a tear between the tissue portions 116, 118.

Figure 13:
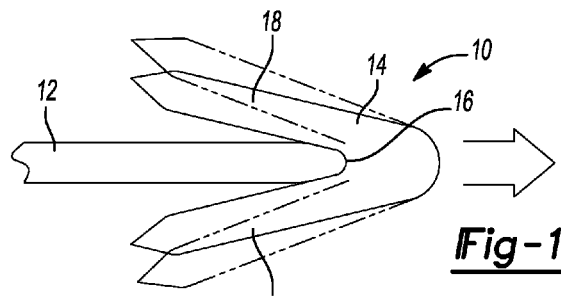
FIG. 13 is a planar view of a tissue engaging member attached to a distal end of a flexible member, with the tissue engaging member deflected radially inward toward the flexible member as the flexible member is inserted into tissue.

FIG. 13 shows the optional deflection of the tissue engaging member 14 as the tissue engaging member 14 is inserted into tissue. The arrow represents a first direction in which the tissue engaging member 14 is inserted. The dashed lines represent the tissue engaging member 14 before the tissue engaging member 14 is inserted into tissue, and the solid lines represent the tissue engaging member 14 after the tissue engaging member 14 is inserted into tissue. As shown, the barbs 18, 20 of the tissue engaging member 14 deflect radially inward toward the flexible member 12 as the tissue engaging member 14 is inserted into tissue. The tissue engaging member 14 can be sufficiently flexible to deflect radially inward toward the flexible member 12 to reduce the effort required to insert the distal end 16 of the flexible member 12 into tissue.

Figure 14:
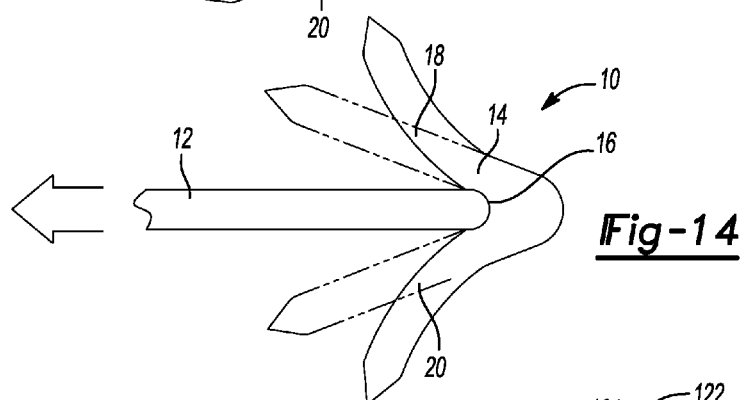
FIG. 14 is a planar view of a tissue engaging member attached to a distal end of a flexible member, with the tissue engaging member deflected radially outward away from the flexible member as a tension force is applied to the flexible member.

FIG. 14 shows the optional deflection of the tissue engaging member 14 as a tension or removal force is applied to the flexible member 12. The arrow represents a second direction in which the removal force is applied. The dashed lines represent the tissue engaging member 14 before the removal force is applied, and the solid lines represent the tissue engaging member 14 after the removal force is applied. As shown, the barbs 18, 20 of the tissue engaging member 14 deflect radially outward from the flexible member 12 as the removal force is applied to the flexible member 12. The tissue engaging member 14 can be sufficiently stiff to prevent further deflection of the barbs 18, 20 and thereby prevent easy removal of the tissue engaging member 14 from tissue. In addition, the barbs 18, 20 can have sharp tips, as shown, that bite into the tissue.

Figure 15:
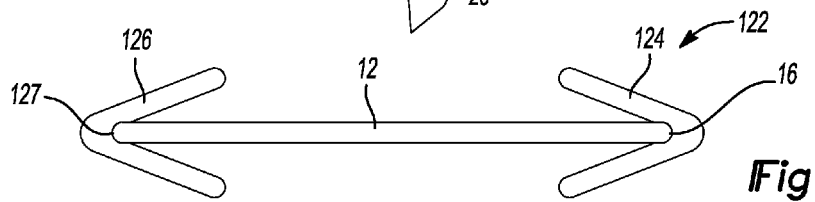
FIG. 15 is a planar view of tissue engaging members attached to opposite ends of a flexible member.

Referring now to FIGS. 15 through 20, a system including a tissue engaging member attached to a distal end of a flexible member can include various connections at a proximal end of the flexible member. FIG. 15 shows a system 122 including a tissue engaging member 124 attached to the distal end 16 of the flexible member 12 and a tissue engaging member 126 attached to a proximal end 127 of the flexible member 12. The tissue engaging member 124 can be inserted into one portion of tissue and the tissue engaging member 126 can be inserted into another portion of tissue to hold the two portions of tissue together. In addition, multiple systems such as the system 122 can be used to hold two portions of tissue together. The two portions of tissue held together can be end-to-end, or the two portions of tissue can be overlapping layers of tissue.

Figure 16A:
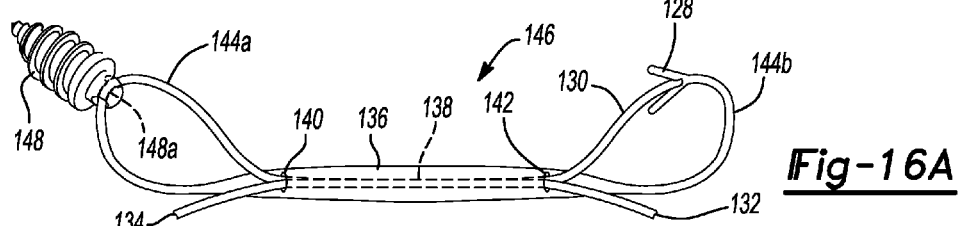
FIG. 16A is a perspective view of a tissue engaging member at a distal end of a flexible member and a self-locking loop at a proximal end of the flexible member, where the self-locking loop is passed through a suture anchor.
Figure 16B:
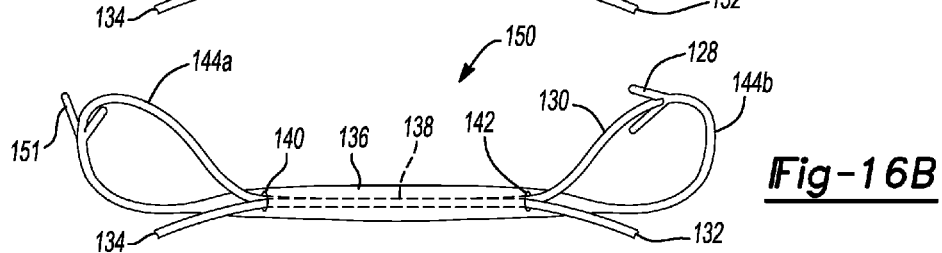
FIG. 16B is a perspective view of a tissue engaging member at a distal end of a flexible member and a self-locking loop at the proximal end of the flexible member, where the self-locking loop is passed through a second tissue engaging member.

FIGS. 16A and 16B show systems that include a tissue engaging member 128 attached to a flexible member 130 forming a self-locking loop. The flexible member 130 has a first end 132 and a second end 134. The flexible member 130 includes a braided body 136 that defines a longitudinal passage 138 extending between a first aperture 140 and a second aperture 142. The first end 132 of the flexible member 130 is passed through the first aperture 140, through the passage 138, and out the second aperture 142. The second end 134 of the flexible member 130 is passed through the second aperture 142, through the passage 138, and out the first aperture 140. In this manner, the flexible member 130 forms two loops 144a, 144b in a bowtie configuration. Reverse movement the flexible member 130 through the passage 136 is resisted once the flexible member 130 is tightened. In this regard, the loops 144a, 144b are self-locking and can be used in place of knots in the flexible member 130.

FIG. 16A shows a system 146 that includes the flexible member 130 arranged in the bowtie configuration, the tissue engaging member 128 attached to the loop 144b, and a suture anchor 148 connected to the loop 144a. The loop 144a can be connected to a suture anchor 148 by passing the loop 144a through a passage 148a in the suture anchor 148. The system 146 can be used to fix soft tissue to bone. For example, the tissue engaging member 128 can be inserted into soft tissue, the suture anchor 148 can be inserted into bone, and the first and second ends 132, 134 of the flexible member 130 can be pulled to lock the loops 144a, 144b.

FIG. 16B shows a system 150 including the tissue engaging member 128 attached to the loop 144b and a tissue engaging member 151 connected to the loop 144a. The system 150 can be used to fix soft tissue to soft tissue. For example, the tissue engaging member 128 can be inserted into one portion of soft tissue, the tissue engaging member 151 can be inserted into another portion of soft tissue, and tension can be applied to the first and second ends 132, 134 to pull the two portions of soft tissue together. Although the flexible member 130 forms two self-locking loops in a bowtie configuration, the flexible member 130 can form more or less loops in various configurations. Further discussion of self-locking loops can be found in commonly assigned U.S. patent application Ser. No. 11/541,505, now U.S. Pat. No. 7,658,751, and U.S. patent application Ser. No. 11/541,506, now U.S. Pat. No. 7,601,165, the disclosures of which are incorporated by reference herein in their entirety.

FIG. 17 shows a system 152 including a suture or flexible member 154 and a tissue engaging member 156 attached to a distal end 158 of the flexible member 154. A proximal end of the flexible member 154 is connected to a suture anchor 160 by, for example, fixing the proximal end of the flexible member 154 within a hollow opening 162 in the suture anchor 160. The proximal end of the flexible member 154 can include a self-locking loop, such as the self-locking loop 136 of FIGS. 16A and 16B, which loops around a shoulder or ledge on the suture anchor 160 within the hollow opening 162 to hold the proximal end of the flexible member 154 in place. The system 152 can be used to fix soft tissue to bone using the suture anchor 160.

FIG. 18 shows braided sutures or flexible members 166, 168, 170, and tissue engaging members 172, 174, 176 attached to distal ends 178, 180, 182 of the flexible members 166, 168, 170 rather than a single tissue engaging member attached to the distal ends 178, 180, 182. The flexible members 166, 168, 170 are connected to a construct 184 including intertwined portions 186, 188, 190 of the flexible members 166, 168, 170. Although the construct 184 is shown as including intertwined portions 186, 188, 190 of the flexible members 166, 168, 170, the construct 184 can be a flexible member having a diameter that is larger than the diameters of the flexible members 166, 168, 170, and the flexible members 166, 168, 170 can extend from the larger-diameter flexible member forming the construct 184.

FIG. 19 shows a system 190 including a suture or flexible member 192 and a tissue engaging member 194 attached to a distal end 196 of the flexible member 192. A proximal end 198 of the flexible member 192 is connected to a tissue reinforcing material 200, such as an allograft patch or Sport-Mesh™ from Biomet Sports Medicine of Warsaw, Ind. The tissue reinforcing material 200 can be placed on tissue such as skin, soft tissue, or bone, and the tissue can grow or thicken into the tissue reinforcing material 200. The tissue reinforcing material 200 can be attached to the tissue using an adhesive, and the tissue reinforcing material 200 can be used to hold portions of tissue together at a defect site. The tissue engaging member 194 can be used to tie soft tissue to the tissue on which the tissue reinforcing material 200 is placed.

FIG. 20 shows a system 202 that includes the flexible member 192 and the tissue engaging member 194 attached to the distal end 196 of the flexible member 192. The proximal end 198 of the flexible member 192 is attached to a tissue adhering material 204 such as an adhesive or blood. The tissue adhering material 204 can couple the proximal end 198 of the flexible member 192 to a tissue 205, and the tissue engaging member 194 can couple the distal end 196 of the flexible member 192 to another tissue (not shown). Although FIGS. 16 through 20 depict tissue engaging members attached to distal ends of flexible members and other elements connected to proximal ends of the flexible members, the tissue engaging members can be attached to the proximal ends of the flexible members and the other elements can be connected to the distal ends of the flexible members. In addition, in FIGS. 1 through 20, any number of tissue engaging members having various shapes and sizes can be used with any of the embodiments in any combination.

Referring now to FIGS. 21 through 26, elongate members including tissue engaging members or barbs radially extending from elongate bodies will now be described. The barbs and the elongate bodies can be made from PEEK, polyethylene, and/or metal. The elongate bodies can be sufficiently stiff to enable insertion of the elongate bodies into tissue.

Figure 21:
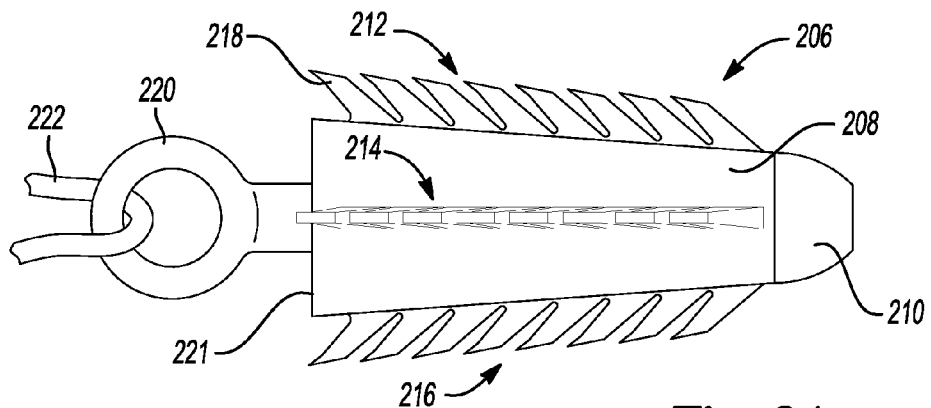
FIG. 21 is a planar view of a first elongate member including a plurality of tissue engaging members extending rearward from a distal end of an elongate body and a suture engaging feature at a proximal end of the elongate body.

FIG. 21 shows an elongate member 206 including a tapered elongate body 208 having a distal end 210 that can be rounded, as shown, to guide the elongate member 206 into a preformed hole in soft tissue, bone, or a suture anchor. Alternatively, the distal end 210 of the elongate body 208 can be pointed to pierce into soft tissue. The elongate body 208 can be 3.5 to 10.0 mm in length and 1 to 3 mm in diameter. In addition, the elongate body 208 can be rigid and therefore may not deflect when inserted into soft tissue or bone.

The elongate member 206 includes a first row of tissue engaging members or barbs 212, a second row of tissue engaging members or barbs 214, and a third row of tissue engaging members or barbs 216. The barbs 212, 214, 216 extend rearward from the distal end 210 of the elongate body 208 at an angle other than parallel to a longitudinal axis of the elongate body 208. Although not shown, the elongate body 208 can include a fourth row of tissue engaging members or barbs on the hidden surface of the elongate body 208 opposite from the second row of barbs 214. In this regard, when viewing the elongate body 208 in a direction toward the distal end 210 of the elongate body 208, the first row of barbs 212, the second row of barbs 214, the third row of barbs 216, and the fourth row of barbs can be axial paths spaced 90 degrees apart around the circumference of the elongate body 208. In addition, the elongate member 206 can include at least 6 to 12 barbs per mm of length of the elongate body 208.

Further, the distance between tips of the barbs can be greater than the distance between bases of the barbs so that tissue or suture is pinched between the barbs as the tissue or suture is forced between the barbs. The tissue or suture may be forced between the barbs when the barbs pierce the tissue or suture or when the barbs engage the tissue or suture without piercing the tissue or suture. In either case, pinching the tissue or suture between the barbs locks the elongate member 206 in the tissue or suture.

The barbs can be sufficiently flexible to deflect radially inward toward the elongate body 208 when the elongate member 206 is inserted into tissue in a first direction to reduce the effort required to insert the elongate member 206 into tissue. In addition, the barbs can be sufficiently rigid and deflect radially outward from the elongate body 208 when a removal force is applied to the elongate member 206 in a second opposite direction to prevent removal of the elongate member 206 from tissue, such as soft tissue or bone. Each of the barbs can include a hooked or pointed end 218 that pierces into tissue to prevent removal of the elongate member 206 from the tissue. The elongate body 208 can remain rigid as the barbs flex radially inward and outward.

The elongate member 206 can also include a suture engaging feature 220, such as an eyelet or a shoulder, which is separate from and attached to a proximal end 221 of the elongate body 208. Alternatively, the elongate body 208 and the suture engaging feature 220 can be integrally formed. For example, the elongate body 208 can define the suture engaging feature 220, which can be a hole formed in the elongate body 208. A suture 222 can be passed through the suture engaging feature 220. The suture engaging feature 220 can be positioned at the proximal end 221 of the elongate body 208, at the distal end 210 of the elongate body 208, or at a location between or beyond the ends 210, 221 of the elongate body 208.

Figure 22:
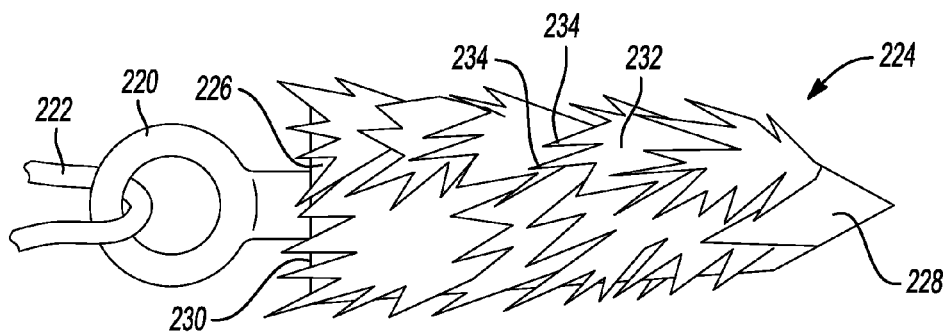
FIG. 22 is a planar view of a second elongate member including a plurality of tissue engaging members extending rearward from a distal end of an elongate body and a suture engaging feature at a proximal end of the elongate body.

FIG. 22 shows an elongate member 224 including an elongate body 226 having a distal end 228 and a proximal end 230. The distal end 228 of the elongate body 226 can be sharpened, as shown, or rounded. The elongate member 224 includes multiple tissue engaging members or leaves 232 extending rearward from the distal end 228 of the elongate body 226. The leaves 232 can include layers of planar members randomly adhered to the elongate body 226 along the length of and about the elongate body 226. The leaves 232 can have multiple jagged protrusions or barbs 234 that pierce into tissue to prevent removal of the elongate member 224 from tissue. The leaves 232 can lie relatively flat against the elongate body 226 unless a removal force is applied to the elongate member 224, in which case the leaves 232 can deflect radially outward to prevent removal of the elongate member 224. The suture engaging feature 220 can be attached to the proximal end 230 of the elongate body 226.

Figure 23:
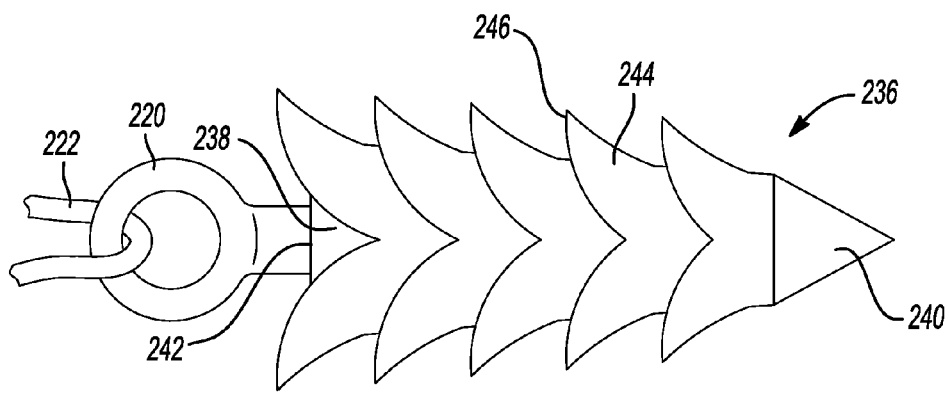
FIG. 23 is a planar view of a third elongate member including a plurality of tissue engaging members extending rearward from a distal end of an elongate body and a suture engaging feature at a proximal end of the elongate body.

FIG. 23 shows an elongate member 236 including an elongate body 238 having a distal end 240 and a proximal end 242. The elongate body 238 includes radially extending tissue engaging members or leaves 244 stacked uniformly along the length of the elongate body 238 to form a pine tree shape. The leaves 244 are flexible and include pointed protrusions or barbs 246 that pierce into tissue when a removal force is applied to the elongate member 236 to prevent removal of the elongate member 236. The distal end 240 of the elongate body 238 is pointed to enable the elongate member 236 to pierce into tissue.

FIG. 24A illustrates an elongate member 248 that includes an elongate body 250 having a distal end 252 and a proximal end 254. The distal end 252 of the elongate body 250 is a pointed or sharp tip that enables the elongate member 248 to pierce into tissue. The elongate body 250 defines a first channel 256 adjacent to the proximal end 254 of the elongate body 250 and a second channel 258 adjacent to the distal end 252 of the elongate body 250. The channels 256, 258 of the elongate body 250 receive an actuator 260 such as a cannulated rod having a closed distal end 261.

A suture 262 can be attached to the actuator 260 such as by press fitting the suture 262 within the actuator 260. The actuator 260 can include multiple sockets 264, and multiple tissue engaging members or barbs 266 can extend through holes 268 in the elongate body 250 and can be pivotally mounted in the sockets 264 of the actuator 260. When the elongate member 248 is inserted into tissue, the barbs 266 can rotate radially inward toward the elongate body 250 until the barbs 266 contact proximal sides of the holes 268. At that point, the barbs 266 can deflect radially inward toward the elongate body 250. The rotation and/or deflection of the barbs 266 decreases the effort required to insert the elongate member 248 into tissue in a first direction.

FIG. 24B illustrates the elongate member 248 with the actuator 260 retracted to extend the barbs 266 radially outward from the elongate body 250 to prevent removal of the elongate member 248 from tissue in a second direction. To retract the actuator 260, a tension force can be applied to the proximal end of the suture 262, as represented by the larger arrow 269-1. The dashed lines represent the proximal-most barbs 266 and the distal end 261 of the actuator 260 before the actuator 260 is retracted. After the actuator 260 is retracted, the barbs 266 rotate radially outward from the elongate body 250 in the direction indicated by the smaller arrows 269-2 until the barbs 266 contact the distal sides of the holes 268 and the elongate body 250. In this position, the barbs 266 prevent removal of the elongate member 248 when the elongate member 248 is inserted into tissue.

FIG. 25 shows an elongate member 270 including a tapered elongate body 272 having a distal end 274 and a proximal end 276. The elongate body 272 can include a first row of radially extending tissue engaging members or barbs 278 and a second opposed row of radially extending tissue engaging members or barbs 280 extending rearward from the distal end 274 of the elongate body 272. The distance between tips of the barbs 278, 280 can be greater than the distance between bases of the barbs 278, 280.

The elongate body 272 can also include a suture engaging portion 281 from which no barbs extend, and the elongate body 272 can define a hole 282 adjacent to the suture engaging portion 281 and the distal end 274 of the elongate body 272. A suture 284 can be routed past the proximal end 276 of the elongate body 272, alongside the suture engaging portion 281 of the elongate body 272, and through the hole 282 in the elongate body 272. Since the suture engaging portion 281 of the elongate body 272 does not have barbs extending therefrom, the suture 284 is allowed to pass freely alongside the elongate body 272. The suture engaging portion 281 of the elongate body 272 can be recessed to ensure that the suture 284 stays within the suture engaging portion 281.

FIG. 26A shows an elongate member 286 including a tapered elongate body 288 having a distal end 290 and a proximal end 292. The elongate body 288 includes a first row of tissue engaging members or barbs 294, a second row of tissue engaging members or barbs 296, a third row of tissue engaging members or barbs 298, a fourth row of tissue engaging members or barbs 300, and a fifth row of tissue engaging members or barbs 302. The elongate body 288 can also include additional rows of tissue engaging members or barbs that are not visible in FIG. 26A but are shown in FIGS. 26B and 26C. The barbs extend rearward from the distal end 290 of the elongate body 288, and the barbs are positioned around the circumference of the elongate body 288 along the length of the elongate body 288. The distance between tips of the barbs can be greater than the distance between bases of the barbs.

A suture engaging feature 304, such as an eyelet, can be positioned distal to the distal end 290 of the elongate body 288, and a suture 306 can be passed through the suture engaging feature 304. The elongate body 288 can have a bullet or round shape, as shown in FIG. 26B, or the elongate body 288 can have a flat shape, as shown in FIG. 26C. Similarly, the elongate bodies shown in FIGS. 21 through 23 and 25 can also have a flat or round shape. In both FIGS. 26B and 26C, the elongate body 288 includes rows of tissue engaging members or barbs that are opposite from and symmetric to the second, third and fourth rows of barbs 296, 298, 300.

Figure 27:
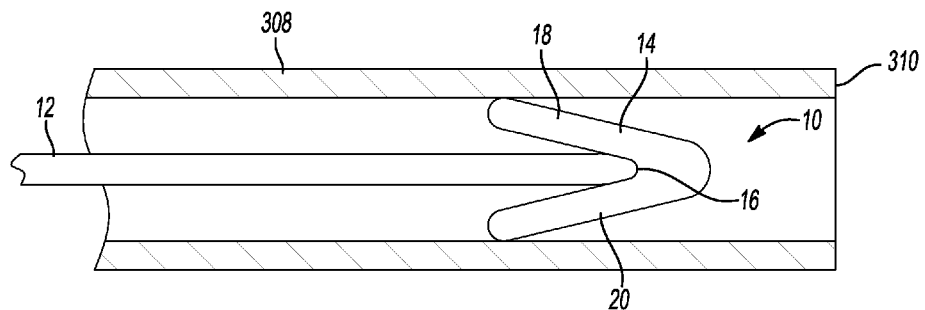
FIG. 27 is a section view of a tissue engaging member attached to a distal end of a suture positioned within a suture delivery tube.

Referring now to FIGS. 27 through 30, various methods of delivering a tissue engaging member and/or an elongate member according to the principles of the present disclosure will now be described. FIG. 27 depicts delivery of the system 10 of FIG. 1 through a tube 308. The tube 308 has a distal end 310 that is open to allow delivery of the flexible member 12 and the tissue engaging member 14 through the distal end 310. The tube 308 can provide structural support for the flexible member 12 to enable insertion of the flexible member 12 and the tissue engaging member 14 into tissue. Although the barbs 18, 20 are shown extending radially outward from the flexible member 12, the inner diameter of the tube 308 can be approximately equal to or only slightly greater than the outer diameter of the flexible member 12, which would force the barbs 18, 20 radially inward toward the flexible member 12 and minimize the opening in the tissue required to insert the tube 308. The tissue engaging member 14 can be pushed into the tissue using a fork or a tube (not shown) inserted between the barbs 18, 20 and the flexible member 20.

Figure 28:
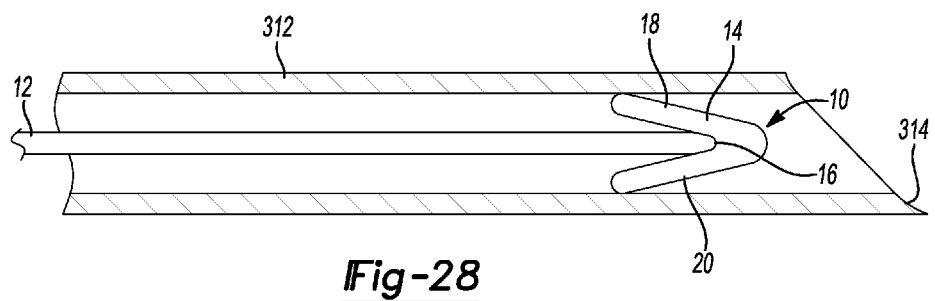
FIG. 28 is a section view of a tissue engaging member attached to a distal end of a suture positioned within a suture delivery tube having a sharp distal end for piercing tissue.

FIG. 28 illustrates a tube 312 having a distal end 314 that is open to allow delivery of the flexible member 12 and the tissue engaging member 14 through the distal end 314. The tube 312 can provide structural support for the flexible member 12 to enable insertion of the flexible member 12 and the tissue engaging member 14 into tissue. In addition, the distal end 314 of the tube 312 has a pointed or sharp tip that enables the tube 312 to pierce into tissue.

Figure 29A:
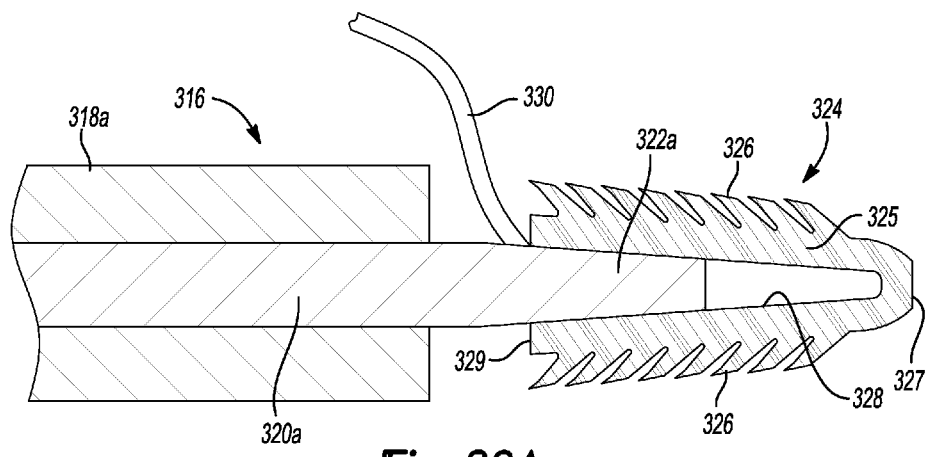
FIG. 29A is a section view of an elongate member mounted on a distal end of a first rod fixed to a first cannula, the elongate member including a plurality of tissue engaging members extending rearward from a distal end of an elongate body and a suture engaging feature through which a suture is passed.

FIG. 29A shows a delivery inserter 316 that includes a cannula 318a and a rod 320a extending through the cannula 318a and having a distal end 322a. An elongate member 324 can be placed over the distal end 322a of the delivery inserter 316. The elongate member 324 includes an elongate body 325 and multiple tissue engaging members or barbs 326 extending radially outward from the elongate body 325 and rearward from a distal end 327 of the elongate body 325. The elongate body 325 defines a hole 328 that extends through a proximal end 329 of the elongate body 325 and at least partially through the elongate body 325. The distal end 322a of the rod 320a is tapered, and the hole 328 in the elongate member 324 is tapered to match the taper of the distal end 322a. A suture 330 can be trapped between the elongate member 324 and the distal end 322a of the rod 320a as the elongate member 324 is slid onto the distal end 322a. Alternatively, the suture 330 can be connected to the elongate member 324 before the elongate member 324 is placed onto the distal end 322a of the rod 320a, such as by looping the suture 330 through or around a suture engaging feature on the elongate member 324.

In operation, a surgeon can hold the cannula 318a and position the elongate member 324 at a desired location within tissue. Once the elongate member 324 is positioned as desired, the surgeon can pull on the cannula 318a and thereby remove the elongate member 324 from the distal end 322a of the rod 320a. When the surgeon pulls on the cannula 318a to retract the delivery inserter 316, the barbs 326 engage tissue to prevent removal of the elongate member 324 and the distal end of the suture 330 from the tissue.

Figure 29B:
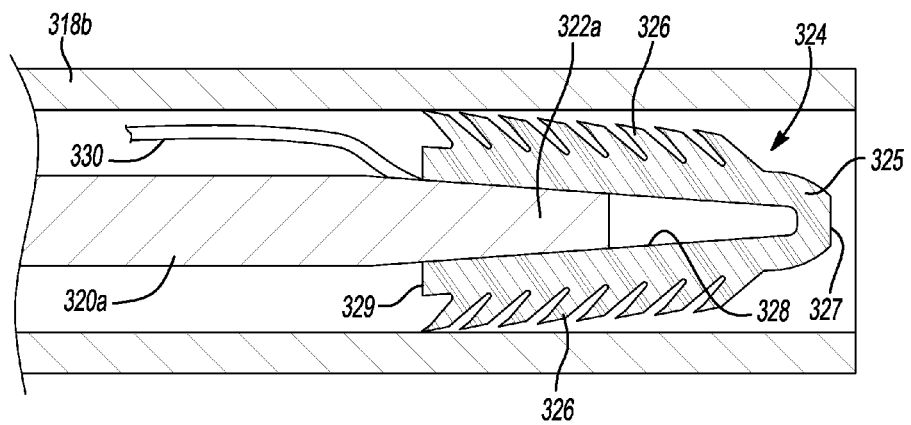
FIG. 29B is a section view of the elongate member of FIG. 29A mounted on the distal end of the first rod and inserted into a second cannula.

FIG. 29B shows a delivery inserter that is similar to the deliver inserter 316 of FIG. 29A except that the cannula 318a is replaced with a cannula 318b, which is sized to receive both the rod 320a and the elongate member 324. In operation, the elongate member 324 is placed onto the distal end 322a of the rod 320a, and the rod 320a is inserted into the cannula 318b. The cannula 318a is then inserted into tissue, such as soft tissue, to deliver the elongate member 324 through the tissue without engaging the elongate member 324 and the tissue. The rod 320a is then used to push the elongate member 324 into tissue, such as soft tissue or bone. The cannula 318b and the rod 320a are then removed from the tissue, leaving the elongate member 324 in the tissue.

Figure 29C:
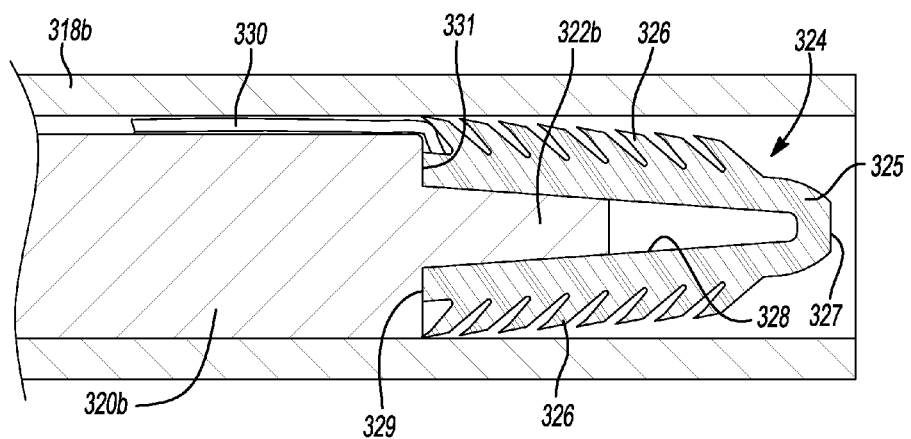
FIG. 29C is a section view of the elongate member of FIG. 29A mounted on a distal end of a second rod and inserted into the second cannula.

FIG. 29C shows a delivery inserter that is similar to the deliver inserter of FIG. 29B except that the rod 320a is replaced with a rod 320b, which includes a distal end 322b and a shoulder 331 at a transition to a distal end 322b. In operation, the elongate member 324 is slid onto the distal end 322 of the rod 320a until the elongate member 324 abuts the shoulder 331 on the rod 320b, and the rod 320a is inserted into the cannula 318b. Then, the elongate member 324 is delivered through tissue using the cannula 318a, the elongate member 324 is pushed into tissue using the rod 320b, and the cannula 318b and the rod 320b are removed from the tissue, as described above.

Figure 30:
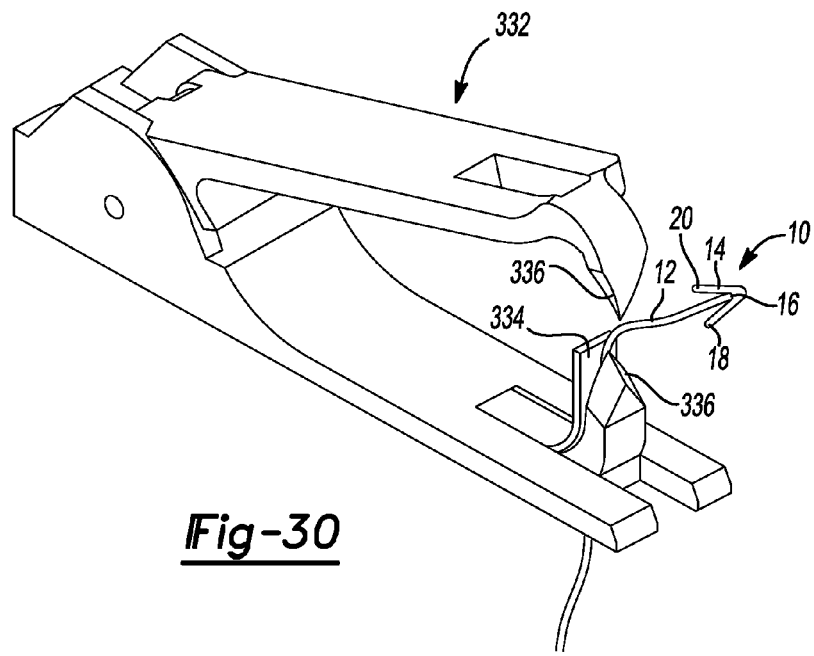
FIG. 30 is a perspective view of a suture passer passing a suture having a distal end to which a tissue engaging member is attached.

FIG. 30 shows a suture passer 332 including a needle 334 that can be extended to insert a suture system into tissue. For illustrations purposes, the suture passer 332 is shown passing the system 10 of FIG. 1. The needle 334 can be sufficiently flexible to pass through the suture passer 332 and sufficiently rigid to guide the system 10 and/or pierce into tissue. The suture passer 332 can include cutting edges 336 that can be used to pierce a hole in tissue before passing a suture system into the tissue. Further discussion of suture passers and methods of delivering sutures into tissue using suture passers can be found in commonly assigned U.S. patent application Ser. No. 11/346,540, U.S. patent application Ser. No. 11/386,074, now U.S. Pat. No. 7,572,265, and U.S. patent application Ser. No. 11/501,171, the disclosures of which are incorporated by reference herein in their entirety. The suture passer 332 is shown for illustration purposes and can be replaced with other suture passers, or combinations thereof, disclosed in the aforementioned patent applications.

Figure 31:
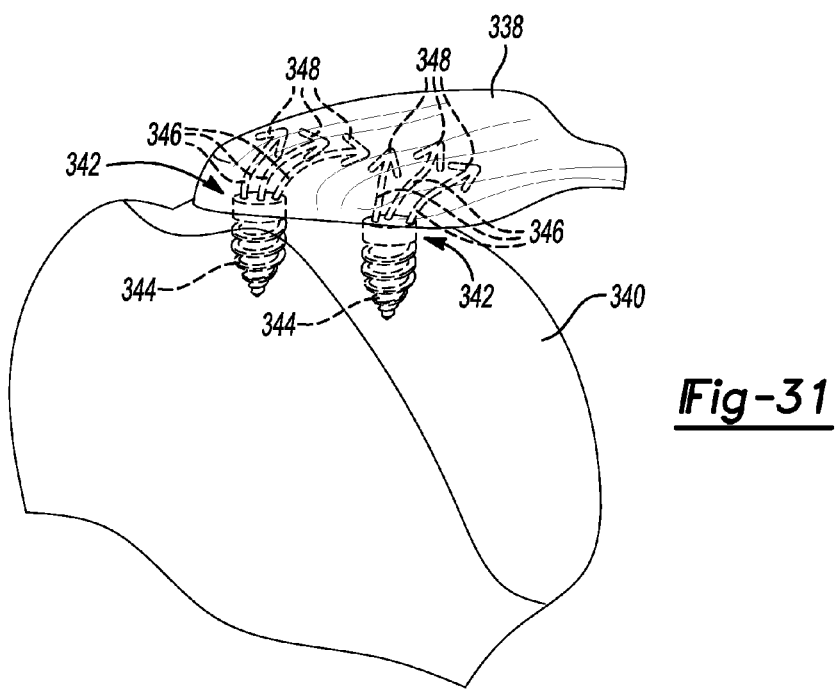
FIG. 31 is a perspective view of a plurality of sutures having distal ends fixed to tissue using a plurality of tissue engaging members, and proximal ends fixed in bone using a plurality of suture anchors.

Referring now to FIGS. 31 through 35, various methods of repairing a defect in tissue using a tissue engaging member according to the principles of the present disclosure will now be described. FIG. 31 shows a tissue repair, such as a rotator cuff repair, in which a tissue 338, such as a tendon or rotator cuff, is attached to a bone 340, such as a humerus, using suture systems 342. The suture systems 342 each include a suture anchor 344 coupled to ends of multiple sutures 346, and tissue engaging members or barbs 348 coupled to the opposite ends of the sutures 346. The sutures 346 extend into the tissue 338 and hold the tissue 338 onto the bone 340. Although two suture systems 342 are shown, more or less suture systems including more or less sutures and tissue engaging members can be used to attach the tissue 338 to the bone 340.

Figures 32A, 32B:
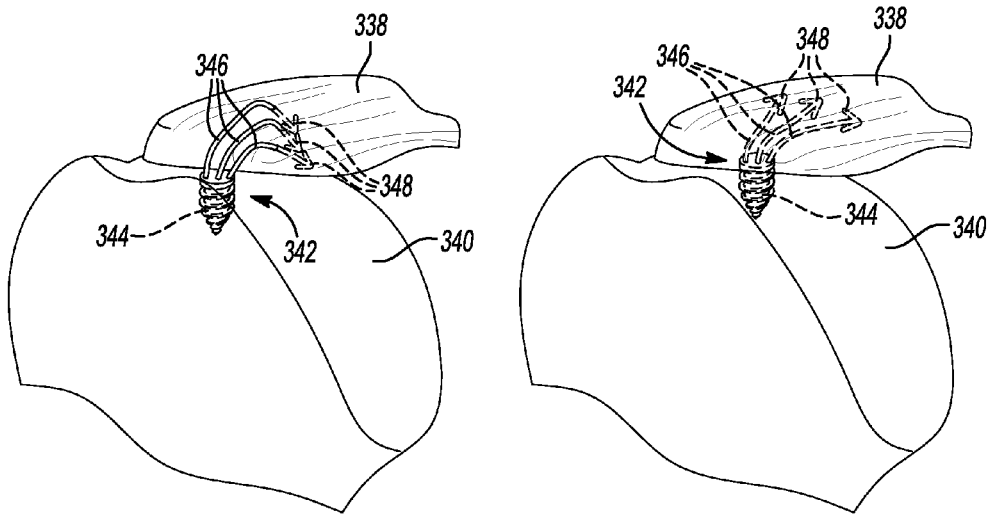
FIG. 32A is a perspective view of a plurality of sutures wrapped around tissue and inserted into tissue, with proximal ends of the plurality of sutures fixed to bone using a suture anchor and distal ends of the plurality of sutures fixed to tissue using a plurality of tissue engaging members.
FIG. 32B is a perspective view of a plurality of sutures extending directly into tissue, with proximal ends of the plurality of sutures fixed to bone using a suture anchor and distal ends of the plurality of sutures fixed to tissue using a plurality of tissue engaging members.

FIGS. 32A and 32B show only one of the suture systems 342 holding the tissue 338 onto the bone 340. In FIG. 32A, the sutures 346 extend from the suture anchor 344 and wrap around the tissue 338 before entering a top surface of the tissue 338. In FIG. 32B, the sutures 346 extend directly from the suture anchor 344 into a bottom surface of the tissue 338. In both figures, the barbs 348 are pushed deeper into the tissue 338 to tension the sutures 346.

Figure 33:
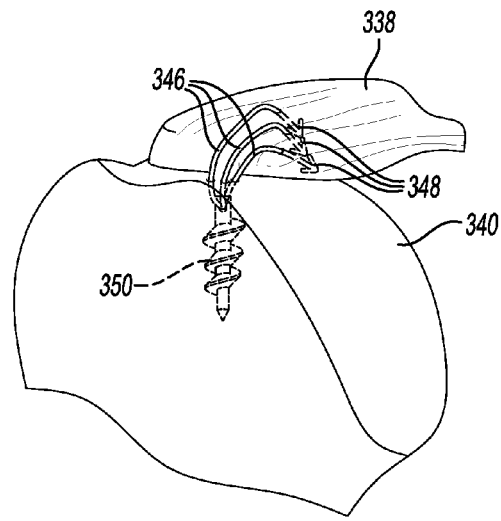
FIG. 33 is a perspective view of a plurality of sutures wrapped around and inserted into tissue, with proximal ends of the sutures attached to a ti screw suture anchor and distal ends of the plurality of sutures fixed in the tissue using tissue engaging members.

FIG. 33 is similar to FIG. 32A except that the suture anchor 344 has been replaced with a suture anchor 350 such as a Ti Screw Suture Anchor from Biomet Sports Medicine of Warsaw, Ind. The suture anchor 350 has a major diameter and a minor diameter that is less than the major diameter. Although only one suture anchor is shown, one or more suture anchors can be coupled to one or more suture and tissue engaging member arrangements to attach the tissue 338 to the bone 340.

Figure 34:
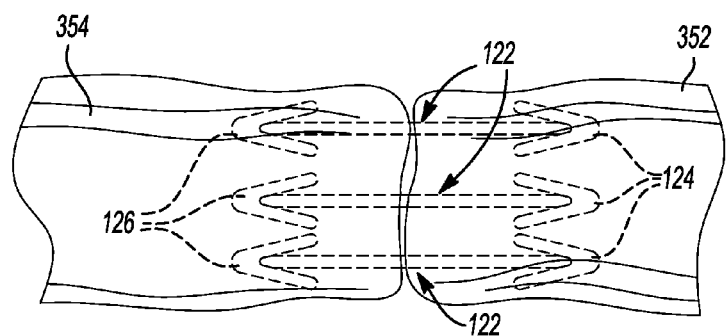
FIG. 34 is a planar view of a tendon repair using a plurality of sutures having opposite ends to which tissue engaging members are attached.

FIG. 34 illustrates a tendon repair using the system 122 of FIG. 15. Tissue portions 352, 354 are positioned end-to-end, and the system 122 is used to hold the ends of the tissue portions 352, 354 together. The tissue portions 352, 354 can be two portions of one torn tendon, two separate tendons, or a tendon and a bone. The tendon portions 352, 354 can be part of an anterior cruciate ligament (ACL) or a posterior cruciate ligament (PCL). Although FIG. 34 shows three duplicates of the system 122 being used to attach the ends of the tendon portions 352, 354, more or less duplicates of the system 122 can be used to attach the ends of the tendon portions 352, 354. The first tissue engaging member 124 of the system 122 is inserted into and engages the tendon portion 352, and the second tissue engaging member 126 of the system 122 is inserted into and engages the tendon portion 354. Tension is applied to the suture 12 by pushing the tissue engaging members deeper into the tendon portions 352, 354.

Figure 35A:
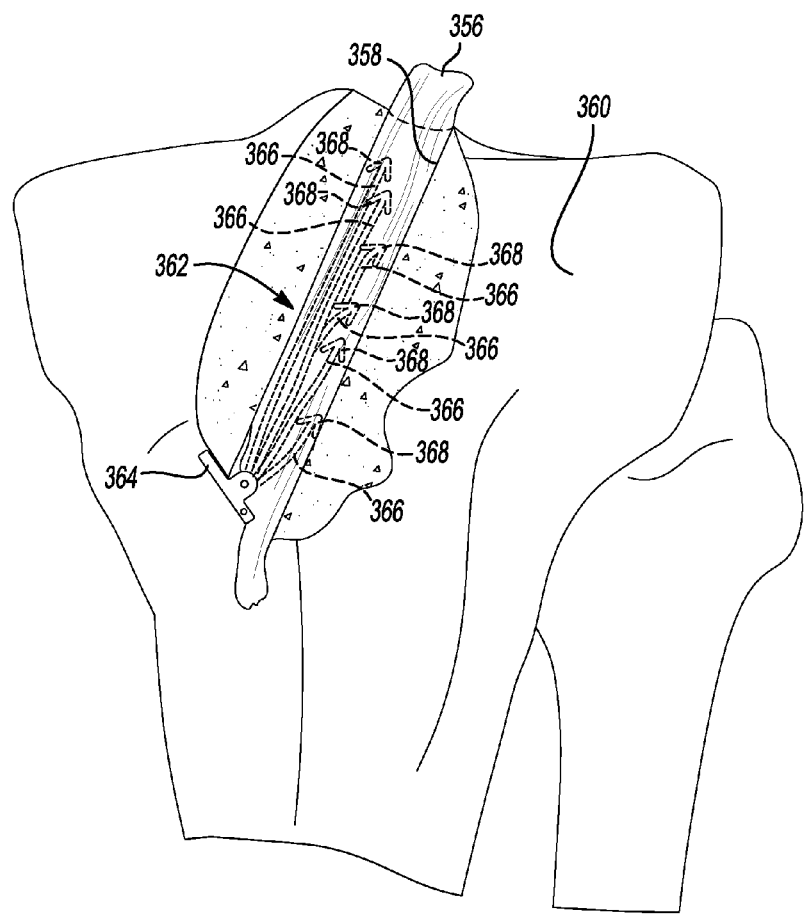
FIG. 35A is a perspective view of an anterior cruciate ligament (ACL) reconstruction in which tissue is fixed within a hole in a tibia using a plurality of sutures having proximal ends attached to a toggle anchor, and distal ends to which a plurality of tissue engaging members are attached.
Figure 35C:
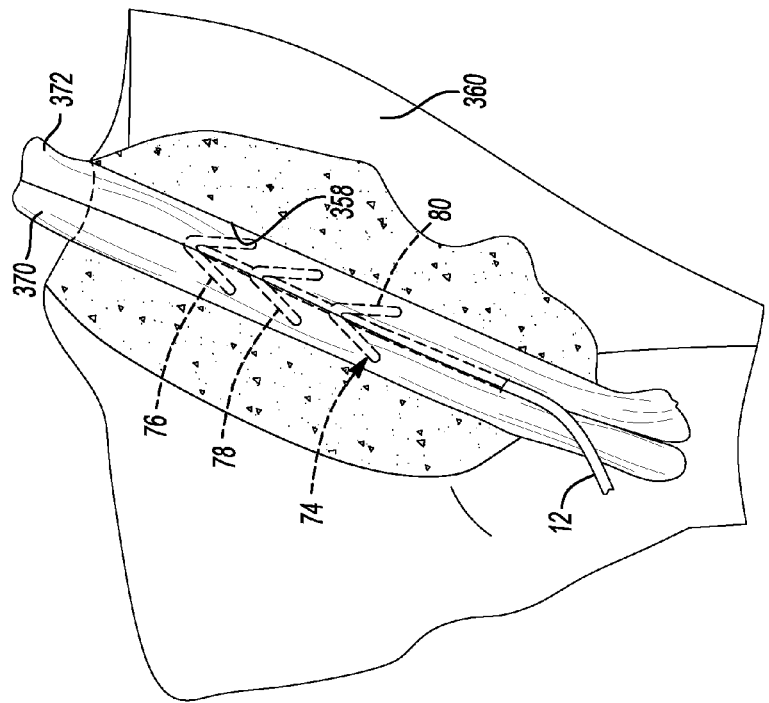
FIG. 35C is a perspective view of an ACL reconstruction in which a plurality of tissue engaging members attached to a suture are piercing two portions of tissue to hold the two portions of tissue together.
Figure 35B:
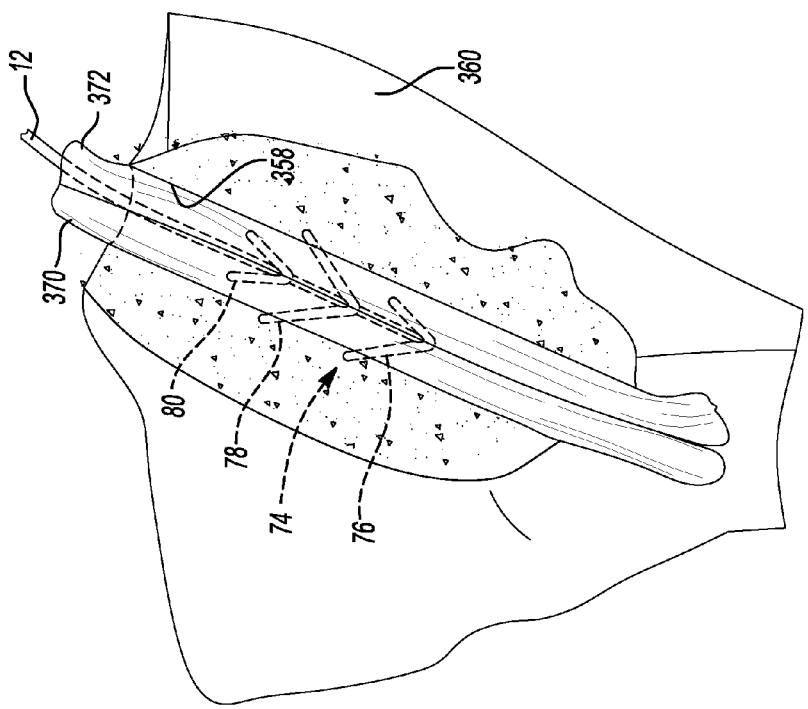
FIG. 35B is a perspective view of an ACL reconstruction in which a plurality of tissue engaging members attached to a suture are piercing through two portions of tissue and into a tibia to hold the two portions of tissue.

FIGS. 35A through 35C illustrate a method of performing an ACL reconstruction using a tissue engaging member according to the principles of the present disclosure. In the ACL reconstruction, a tissue 356, such as graft, is inserted into a hole 358 in a tibia 360. A system 362 includes a toggle anchor 364 positioned at the lower end of the hole 358 and coupled to ends of multiple sutures 366, and tissue engaging members or barbs 368 attached to the opposite ends of the sutures 366. The tissue engaging members 368 engage the tissue 356 to hold the tissue 356 within the hole 358 in the tibia 360. Although FIGS. 35A through 35C shows the ACL reconstruction on the tibia side, the ACL reconstruction on the femoral side can be performed in a similar manner using the system 362.

FIGS. 35B and 35C show tissue portions 370, 372 held together by the system 74 of FIG. 7. One of the barbs in each of the tissue engaging members 76, 78, 80 is engaging the tissue portion 370, and the other one of the barbs in the tissue engaging members 76, 78, 80 is engaging the tissue portion 372. In FIG. 35B, the barbs of the tissue engaging members 76, 78, 80 extend downward through the tissue portions 370, 372 and into the tibia 360. In FIG. 35C, the barbs of the tissue engaging members 76, 78, 80 extend upward into the tissue portions 370, 372 without penetrating the tibia 360. In this regard, the system 74 can be used to attach the tissue portions 370, 372 together. In addition, although only two tissue portions are shown, the tissue portions 370, 372 can be a four bundle graft, and the system 74 can be used in place of a whip stitch to secure the four bundle graft together.

Figure 36:
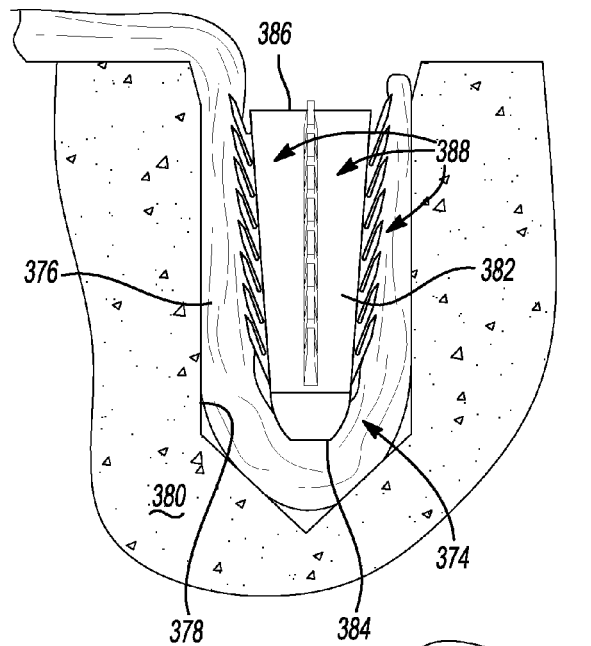
FIG. 36 is a planar view of an elongate member inserted into a hole in bone, the elongate member including a plurality of tissue engaging members engaging tissue and the bone to hold the tissue in the hole.

Referring now to FIGS. 36 through 40, various methods of repairing defects in tissue using an elongate member according to the principles of the present disclosure will now be described. FIG. 36 shows an elongate member 374 holding a tissue 376 within a hole 378 in a bone 380. The elongate member 374 can be used without a suture to hold the tissue 376 within the hole 378 in the bone 380. The elongate member 374 includes a tapered elongate body 382 having a distal end 384 and a proximal end 386, and multiple tissue engaging members or barbs 388 extending rearward from the distal end 384 of the elongate body 382. The barbs 388 engage the tissue 376 and the bone 380 to hold the tissue 376 within the hole 378 in the bone 380.

Figure 37:
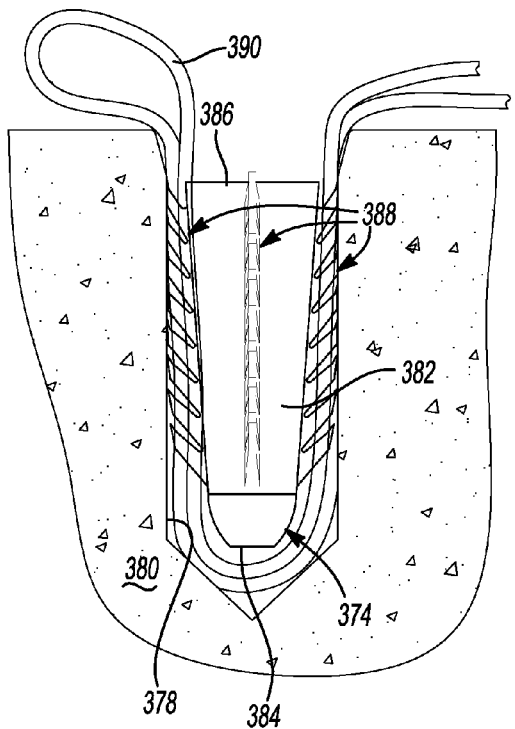
FIG. 37 is a planar view of an elongate member inserted into a hole in bone, the elongate member including a plurality of tissue engaging members engaging a suture and the bone to hold the suture in the hole.

FIG. 37 shows the elongate member 374 engaging a suture 390 to anchor the suture 390 within the hole 378 in the bone 380. The barbs 388 of the elongate member 374 can pierce through the suture 390 and into the bone 380 to hold the suture 390 within the hole 378 in the bone 380. Alternatively, the elongate member 374 can trap the suture 390 within the hole 378 in the bone 380 even when the barbs 388 do not pierce into the suture 390. In either case, the elongate member 374 can function as a suture anchor.

Figure 38:
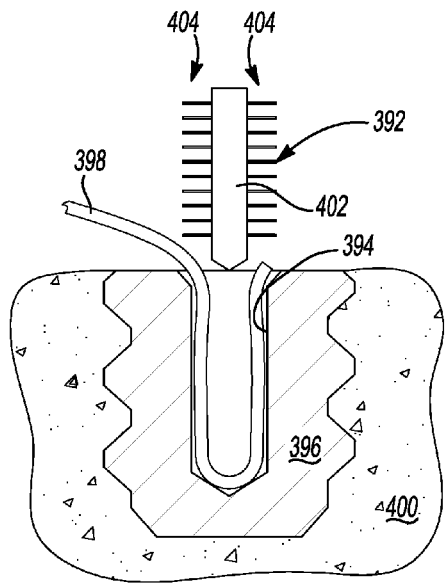
FIG. 38 is a planar view of an elongate member being inserted into a proximal end of a cannulated suture anchor fixed in tissue, the elongate member including a plurality of tissue engaging members for engaging a suture within the cannulated suture anchor to fix the suture to the tissue.

FIG. 38 shows an elongate member 392 shaped similar to a pipe cleaner and being inserted into a hole 394 in a suture anchor 396 fixed in a bone 400 to trap a suture 398 within the hole 394. The elongate member 392 includes an elongate body 402 and tissue engaging members or barbs 404 extending radially from the elongate body 402. The barbs 404 can be attached around the circumference of the elongate body 402 in uniform, straight axial lines or in a random fashion. The barbs 404 engage the suture 398 and the suture anchor 396 to hold the suture 398 within the hole 394 in the suture anchor 396. When the elongate member 392 is inserted within the hole 394, the barbs 404 can extend rearward from the distal end of the elongate body 402 (FIG. 39).

FIG. 39 shows the elongate member 392 inserted into the hole 394 in the suture anchor 396. FIG. 39 is similar to FIG. 38 except that the elongate body 402 defines a hole 406 extending longitudinally through the elongate body 402 and the suture 398 is passed through the hole 406 and around one side of the elongate member 406. When the elongate member 392 is inserted into the hole 394 in the suture anchor 396, the barbs 404 engage the suture anchor 396 and the suture 398 to anchor the suture 398 to the bone 400. Although the suture engaging feature 406 is shown at the proximal end of the elongate member 392, the suture engaging feature 406 can be positioned at the distal end of the elongate member 392 or at any other suitable location along the length of the elongate member 392.

FIG. 40 is similar to FIG. 39 except that a suture engaging feature 407, such as an eyelet, is attached to the proximal end of the elongate member and a suture 398 is passed through the suture engaging feature 407. Additionally, a bracket 408 is attached to the elongate body 402 of the elongate member 392, and a bracket 410 is attached to the suture anchor 396 within the hole 394 in the suture anchor 396. Before the elongate member 392 is inserted into the hole 394 in the suture anchor 396, the elongate member 392 can be oriented so that the bracket 408 does interfere with the bracket 410. Once the elongate member 392 is completely inserted into the hole 394, the elongate member 392 can be rotated to engage the brackets 408, 410 in order to prevent removal of the elongate member 392 from the hole 394 in the suture anchor 396.

The methods for using elongate members discussed above can apply to other elongate members discussed above, or variations thereof, where appropriate. For example, the elongate member 206 of FIG. 21 can be used in a similar manner as the elongate member 392 of FIG. 39. In addition, various features of the elongate members discussed above can be interchangeable. For example, the barbs 212, 214, 216 can extend perpendicular to the longitudinal axis of the elongate body 208 of FIG. 21 just as the barbs 404 extend perpendicular to the longitudinal axis of the elongate body 402 of FIG. 39.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same can also be varied in many ways. Such variations are not to be regarded as a departure from the disclosure, and all such modifications are intended to be included within the scope of the disclosure.

What is claimed is:

1. An elongate member, comprising:
   an elongate body to which a suture engaging feature is fixed; and
   a tissue engaging member protruding from the elongate body at an angle other than parallel to a longitudinal axis of the elongate body, wherein the tissue engaging member includes a plurality of barbs extending from at least two different axial positions along a length of the elongate body, and wherein at least one of the plurality of barbs has a base, a tip, and opposite planar side surfaces, the at least one barb having a width between the opposite planar side surfaces that is less than its height from the base to the tip in a direction transvers to the length of the elongate body, wherein the height is measured perpendicular to a surface formed where the base connects to a tapered side of the elongate body.

2. The elongate member of claim 1, wherein the plurality of barbs are aligned in axial rows extending along the length of the elongate body and spaced apart about a perimeter of the elongate body, and wherein the opposite planar side surfaces extend along the axial rows.

3. The elongate member of claim 2, wherein:
the plurality of barbs aligned in axial rows includes three axial rows spaced about the perimeter of the elongate body;
the plurality of barbs extend radially outward from the elongate body;
each of the plurality of barbs includes a base extending from the elongate body toward a proximal end of the elongate body, a pointed tip extending from the base and toward the proximal end of the elongate body, and opposite planar side surfaces; and
a first distance between the side surfaces at the tip is greater than a second distance between the side surfaces at the base.

4. The elongate member of claim 2, wherein the plurality of barbs aligned in axial rows includes four axial rows equally spaced about the perimeter of the elongate body, wherein the plurality barbs extend radially outward from the elongate body.

5. The elongate member of claim 1, further comprising an actuator operable to actuate the tissue engaging member relative to the elongate body.

6. The elongate member of claim 1, wherein the tissue engaging member includes at least two barbs aligned in at least one row extending along a length of the elongate body, the barbs extending rearward from a distal end of the elongate body, and wherein a first distance between tips of the at least two barbs is greater than a second distance between bases of the at least two barbs.

7. The elongate member of claim 1, wherein the elongate body and tissue engaging member is formed from at least one of PEEK, polyethylene, and metal.

8. The elongate member of claim 1, wherein the elongate body is a tapered elongate body extending from a proximal end to a distal end having a rounded distal tip.

9. The elongate member of claim 8, wherein the tissue engaging member includes a plurality of rows of tissue engaging members extending axially from the proximal end to the distal end, where each row includes a plurality of tissue engaging members extending radially out from the elongate body.

10. The elongate member of claim 9, wherein the plurality of rows includes four rows of tissue engaging members, each row spaced 90° apart around the circumference of the elongate body.

11. The elongate member of claim 10, further comprising a suture engaging eyelet extending from the proximal end of the elongate body.

12. The elongate member of claim 11, wherein each tissue engaging member includes a barb having a tip extending proximally toward the proximal end and a base coupled to the tapered body.

13. The elongate member of claim 2, wherein each axial row having the plurality of barbs is spaced about a smooth tapered body of the elongate body.

14. The elongate member of claim 1, wherein the at least one barb has a proximal surface facing in a direction that extends toward the elongate body.

15. An elongate member, comprising:
an elongate body defining a hole for receiving a suture; and
a plurality of barbs extending radially outward from the elongate body and extending rearward from a distal end of the elongate body,
wherein the elongate body is rigid and the plurality of barbs extend from at least two different axial positions along a length of the elongate body,
wherein at least one of the plurality of barbs has a base and a tip, a longitudinal axis of the base extending from the elongate body at a first angle relative to a longitudinal axis of the elongate body, a longitudinal axis of the tip extending from the base at a second angle relative to the longitudinal axis that is different from the first angle, and
wherein each barbs of the plurality of barbs includes a width measured perpendicular to the longitudinal axis of the base that is less than a height extending radially outward from the elongate body.

16. The elongate member of claim 15, wherein the plurality of barbs have a stiffness that causes the barbs to deflect toward the elongate body as the elongate body is inserted into tissue and to deflect away from the elongate body as a removal force is applied to the elongate body, and wherein the elongate body is configured to remain rigid while the plurality of barbs flex.

17. The elongate member of claim 15, wherein the elongate body has bullet shape and defines a suture engaging eyelet that is positioned at a proximal end of the elongate body and that defines the hole.

18. The elongate member of claim 15, wherein the elongate body is a tapered elongate body extending from a proximal end to a distal end having a rounded distal tip.

19. The elongate member of claim 18, wherein the plurality of barbs includes a plurality of rows of barbs extending axially from the proximal end to the distal end, where each row includes a plurality of barbs extending radially out from the elongate body.

20. The elongate member of claim 19, wherein each of the plurality of barbs is configured to be sufficiently flexible to deflect radially inward toward the elongate body when the elongate body is inserted into tissue in a first direction to reduce the effort required to insert the elongate body into the tissue and configured to be sufficiently rigid to deflect radially outward from the elongate body when a removal force is applied to the elongate body in a second opposite direction to prevent removal of the elongate body from the tissue.

21. The elongate member of claim 20, wherein each barb includes a hooked end configured to pierce the tissue to prevent removal of the elongate body from the tissue, the hooked end including a pointed tip that is angled rearward relative to a longitudinal axis of the base of each barb.

22. An elongate member comprising:
an elongate body extending from a proximal end to a distal end;
a suture engaging eyelet extending from a proximal end of the elongate body; and
a plurality of tissue engaging barbs radially extending from the elongate body wherein the elongate body is rigid and the plurality of barbs are fixed and flexible, where the plurality of barbs are aligned in a plurality of axially extending rows extending from the proximal end to the distal end of the elongate body, where each row is spaced about the circumference of the elongate body, where each row includes at least two axially adjacent barbs and where at least two axially adjacent barbs in at least one of the rows define a u-shaped gap therebetween, and wherein a longitudinal axis of the u-shaped gap extends rearward toward a proximal end of the elongate body, and
wherein each tissue engaging barb of the plurality of tissue engaging barbs includes a base width measured perpendicular to a respective axially extending row that is less than a height measured radially outward from the surface of the elongate member.

23. The elongate member of claim 22, wherein the plurality of rows includes four rows each having a plurality of barbs and each row spaced 90° apart about the circumference of the elongate body.

24. The elongate member of claim 23, wherein the elongate body is a tapered elongate body extending from the proximal end to the distal end having a rounded distal tip.

25. The elongate member of claim 24, wherein each barb extends rearward from the distal end of the elongate body and wherein a first distance between tips of two adjoining barbs is greater than a second distance between bases of the adjoining barbs to configure the barbs to pinch tissue between the adjoining barbs to lock the elongate body in tissue.

26. The elongate member of claim 23, wherein the elongate body has a bullet shape.

27. The elongate member of claim 23, wherein the plurality of barbs have a stiffness that causes the barbs to deflect toward the elongate body as the elongate body is inserted into tissue and to deflect away from the elongate body as a removal force is applied to the elongate body, and wherein the elongate body is configured to remain rigid while the plurality of barbs flex.

28. The elongate member of claim 27, wherein each barb includes a hooked end configured to pierce the tissue to prevent removal of the elongate body from the tissue.

29. The elongate member of claim 22, wherein each of the plurality of barbs includes a proximal surface, a distal surface and opposite planar side surfaces extending between the proximal surface and the distal surface.

\* \* \* \* \*